United States Patent
Wahlström et al.

(10) Patent No.: US 10,287,316 B2
(45) Date of Patent: May 14, 2019

(54) PROCESS FOR PREPARATION OF NITROGEN MUSTARD DERIVATIVES

(71) Applicant: Oncopeptides AB, Stockholm (SE)

(72) Inventors: Niklas Håkan Wahlström, Malmö (SE); Johan Anders Wennerberg, Malmö (SE)

(73) Assignee: Oncopeptides AB, Stockholm (SE)

( * ) Notice: Subject to any disclaimer, the term of this patent is extended or adjusted under 35 U.S.C. 154(b) by 0 days.

(21) Appl. No.: 15/572,300

(22) PCT Filed: May 6, 2016

(86) PCT No.: PCT/EP2016/060242
§ 371 (c)(1),
(2) Date: Nov. 7, 2017

(87) PCT Pub. No.: WO2016/180740
PCT Pub. Date: Nov. 17, 2016

(65) Prior Publication Data
US 2018/0148473 A1    May 31, 2018

(30) Foreign Application Priority Data
May 8, 2015    (GB) .................................. 1507903.1

(51) Int. Cl.
| | | |
|---|---|---|
| *C07K 1/00* | (2006.01) | |
| *A61K 38/00* | (2006.01) | |
| *C07K 5/065* | (2006.01) | |
| *C07C 205/06* | (2006.01) | |
| *C07C 227/18* | (2006.01) | |
| *C07C 229/42* | (2006.01) | |
| *C07C 231/02* | (2006.01) | |
| *C07C 231/12* | (2006.01) | |

(Continued)

(52) U.S. Cl.
CPC ........ *C07K 5/06078* (2013.01); *C07C 227/18* (2013.01); *C07C 231/02* (2013.01); *C07C 231/12* (2013.01); *C07C 237/20* (2013.01); *C07C 237/22* (2013.01); *C07C 269/06* (2013.01); *C07C 271/14* (2013.01); *C07C 271/20* (2013.01); *C07C 271/22* (2013.01); *C07K 1/006* (2013.01); *A61K 38/00* (2013.01); *C07C 205/06* (2013.01); *C07C 229/42* (2013.01); *Y02P 20/55* (2015.11)

(58) Field of Classification Search
None
See application file for complete search history.

(56) References Cited

U.S. PATENT DOCUMENTS

| | | | | |
|---|---|---|---|---|
| 2004/0097421 A1* | 5/2004 | Lewensohn | ........ | C07K 5/06191 560/41 |
| 2011/0190509 A1* | 8/2011 | Chen | ..................... | C07C 233/15 548/306.4 |

(Continued)

FOREIGN PATENT DOCUMENTS

| | | |
|---|---|---|
| CN | 101100440 A | 1/2008 |
| WO | 01/96367 A1 | 12/2001 |

(Continued)

OTHER PUBLICATIONS

Search Report, dated Feb. 10, 2016, in connection with GB Application No. GB1507903.1.

(Continued)

*Primary Examiner* — Amy C Bonaparte
(74) *Attorney, Agent, or Firm* — Biospark Intellectual Property Law

(57) ABSTRACT

The present invention provides a process for the production of compound (III) or a deprotected product thereof: comprising reacting compound (II) with chloroacetic acid, in the presence of a reducing agent; wherein PG is a protecting group and R is OH in a suitably protected form or (A). The invention further provides intermediate compounds formed in the process of the invention, and processes for the production of intermediate compounds.

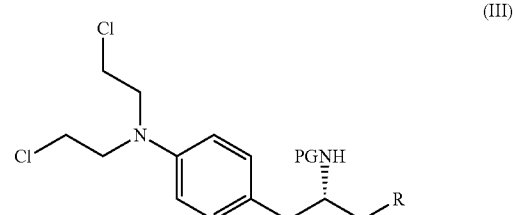

(III)

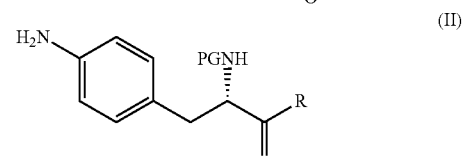

(II)

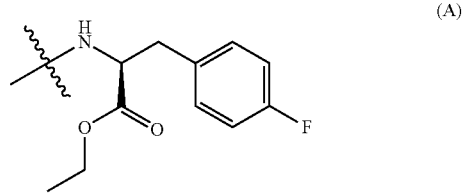

(A)

26 Claims, No Drawings

(51) Int. Cl.
*C07C 237/20* (2006.01)
*C07C 237/22* (2006.01)
*C07C 269/06* (2006.01)
*C07C 271/14* (2006.01)
*C07C 271/20* (2006.01)
*C07C 271/22* (2006.01)

(56) References Cited

U.S. PATENT DOCUMENTS

| 2013/0079383 | A1 | 3/2013 | Bennett et al. |
| 2014/0128462 | A1 | 5/2014 | Spira et al. |
| 2015/0335578 | A1 | 11/2015 | Spira et al. |
| 2016/0271065 | A1 | 9/2016 | Spira et al. |
| 2017/0049894 | A1 | 2/2017 | Spira et al. |

FOREIGN PATENT DOCUMENTS

| WO | 2006/127584 A1 | 11/2006 |
| WO | 2014/141294 A2 | 9/2014 |
| WO | WO 2014/191426 | * 12/2014 |

OTHER PUBLICATIONS

International Search Report and Written Opinion, dated Jul. 20, 2016, in connection with PCT International Application No. PCT/EP2016/060242.

Chauhan D., et al., 2013, "In Vitro and In Vivo Antitumor Activity of a Novel Alkylating Agent, Melphalan-Flufenamide, against Multiple Myeloma Cells," Clin Cancer Res. 19(11): 3019-3031.

Chen, J., et al., 2011, "Discovery of a Novel, Efficient, and Scalable Route to Bendamustine Hydrochloride: The API in Treanda," Org. Process Res. Dev. 15: 1063-1072.

Larden, D. W., et al., 1999, "Synthesis of ▯-Aminoacyl[1] Derivatives of Melphalan for Use in Antibody Directed Enzyme Pro-drug Therapy," Tetrahedron, 55: 3265-3276.

Larden, D. W., et al., 1996, "Synthesis of N-▯-Aminoacyl Derivatives of Melphalan for Potential Use in Drug Targeting," Tetrahedron Letters, 37(42): 7581-7582.

Kupczyk-Subotkowska, L., et al., 1997, "Modulation of Melphalan Resistance in Glioma Cells with a Peripheral Benzodiazepine Receptor Ligand-Melphalan Conjugate", J. Med. Chem. 40: 1726-1730.

Rapp, M. et al., 2003, "Synthesis and in Vivo Biodisposition of [$^{14}$C]-Quaternary Ammonium-Melphalan Conjugate, a Potential Cartilage-Targeted Alkylating Drug," Bioconjugate Chem. 14: 500-506.

Wickström, M., et al., 2007, "The novel melphalan prodrug J1 inhibits neuroblastoma growth in vitro and in vivo," Mol Cancer Ther. 6(9): 2409-2417.

* cited by examiner

PROCESS FOR PREPARATION OF NITROGEN MUSTARD DERIVATIVES

FIELD OF THE INVENTION

The present invention relates to an improved process for preparing melflufen, or a salt thereof, and melphalan, or a salt thereof. The invention further provides novel intermediate compounds formed in the process of the invention.

BACKGROUND OF THE INVENTION

Alkylating agents, such as drugs derived from nitrogen mustard, that is bis(2-chloroethyl)amine derivatives, are used as chemotherapeutic drugs in the treatment of a wide variety of cancers. Melphalan, or p-bis-(2-chloroethyl)-amino-L-phenylalanine (compound (Id), CAS No. 148-82-3), is an alkylating agent which is a conjugate of nitrogen mustard and the amino acid phenylalanine (U.S. Pat. No. 3,032,584). Melphalan is used clinically in the treatment of metastatic melanomas, but has limited efficacy, dose-limiting toxicities and resistance can develop.

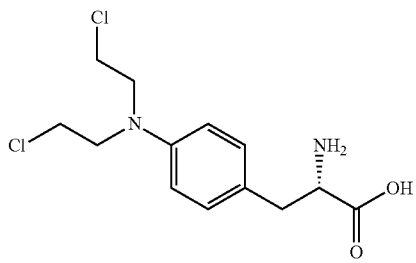

(Id)

Melphalan flufenamide ethyl ester (L-melphalanyl-L-p-fluorophenylalanine ethyl ester, melflufen, compound (Ib)) is a derivative of melphalan conjugated to the amino acid phenylalanine, creating a dipeptide (WO 01/96367):

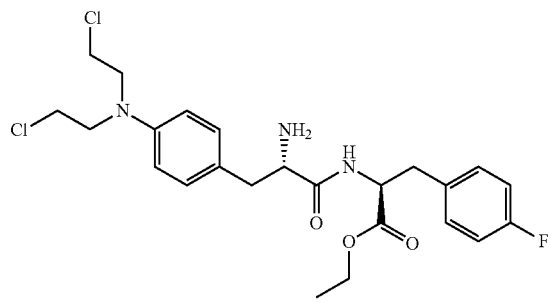

(Ib)

The monohydrochloride salt of melflufen (L-melphalanyl-L-p-fluorophenylalanine ethyl ester monohydrochloride; hydrochloride salt of (Ib); CAS No. 380449-54-7) is referred to as melflufen hydrochloride.

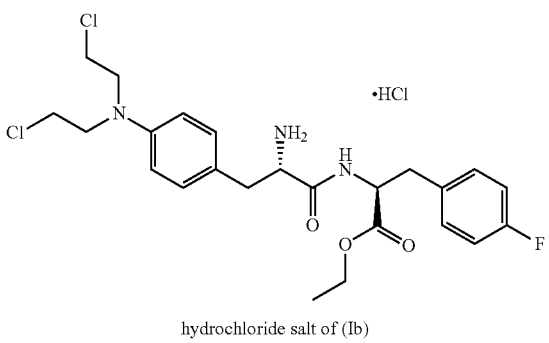 [SMILES: CCOC(=O)[C@H](Cc1ccc(F)cc1)NC(=O)[C@@H](N)Cc1ccc(N(CCCl)CCCl)cc1 ; Cl]

hydrochloride salt of (Ib)

When studied in cultures of human tumor cells representing approximately 20 different diagnoses of human cancers, including myeloma, melflufen showed 50- to 100-fold higher potency compared with that of melphalan (http://www.oncopeptides.se/products/melflufen/accessed 26 Mar. 2015). Data disclosed in Arghya, et al, abstract 2086 "A Novel Alkylating Agent Melphalan Flufenamide Ethyl Ester Induces an Irreversible DNA Damage in Multiple Myeloma Cells" (2014) 5th ASH Annual Meeting and Exposition, suggest that melflufen triggers a rapid, robust and irreversible DNA damage, which may account for its ability to overcome melphalan-resistance in multiple myeloma cells. Melflufen is currently undergoing phase I/IIa clinical trials in multiple myeloma.

A process for preparing melflufen in hydrochloride salt form is described in WO 01/96367, and is illustrated in Scheme 1, below. In that process N-tert-butoxycarbonyl-L-melphalan is reacted with p-fluorophenylalanine ethyl ester to give N-tert-butoxycarbonyl-L-melphalanyl-L-p-fluorophenylalanine ethyl ester. After purification by gradient column chromatography the yield of that step is 43%.

Scheme 1. Current route to melflufen (in hydrochloride salt form)

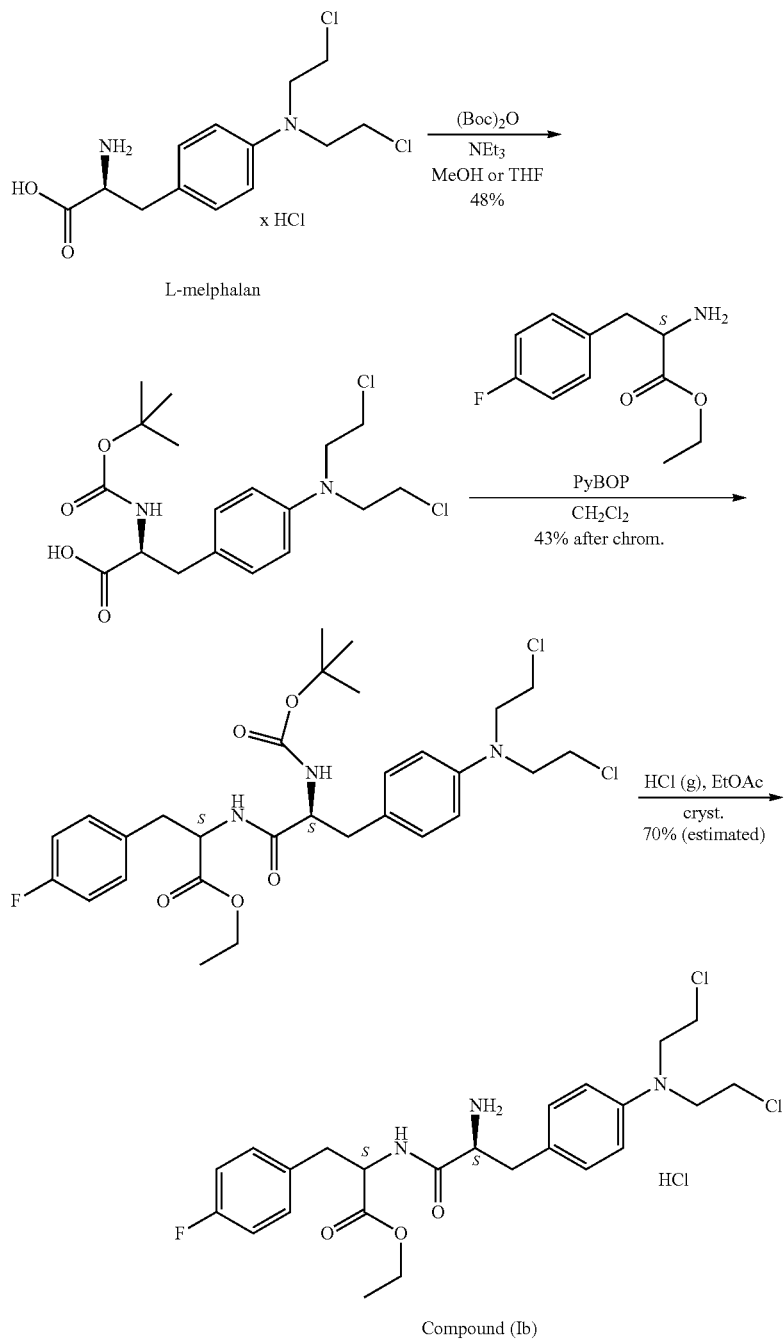

Compound (Ib)

As shown in Scheme 1, the known process for preparing melflufen (in hydrochloride salt form) uses the cytotoxic agent melphalan as a starting material, and melflufen is synthesised in a multistep sequence. Melphalan is highly toxic, thus the staring materials and all of the intermediates, and also the waste stream generated, are extremely toxic. That is a major disadvantage in terms of safety, environmental impact and cost when using the process on a large scale. Therefore, an improved and safer method is highly desired, especially for production of melflufen on a large scale. Further, the purity of commercially available melphalan is poor due to its poor stability, the yield in each step of the process is poor, and purity of the final product made by the known process is not high.

A process for preparing melphalan is described in WO 2014/141294. In WO 2014/141294 the step to introduce the bis(2-chloroethyl) group into the molecule comprises conversion of a primary phenyl amine to a tertiary phenyl amine diol, by reaction with ethylene oxide gas. This gives a 52.6% yield. The amine diol is then converted to a bis(2-chloroethyl) phenylamine by reaction with phosphoryl chloride. Using ethylene oxide, or chloroethanol, to convert an aromatic amine to the corresponding bis-(2-hydroxyethyl) amine, followed by chlorination of that intermediate, is a common technique for producing aromatic bis-(2-chloroethyl) amines. It is also known to start from a chloroarene and let it undergo a SNAr-reaction with diethanolamine. The present inventors have applied those methods to produce melflufen (in its salt form), shown in Scheme 2 below.

In summary, none of these routes were found to be suitable for large scale production of high purity melflufen. They do not work well for the synthesis of melflufen, resulting in poor yields and are inefficient. Further, the

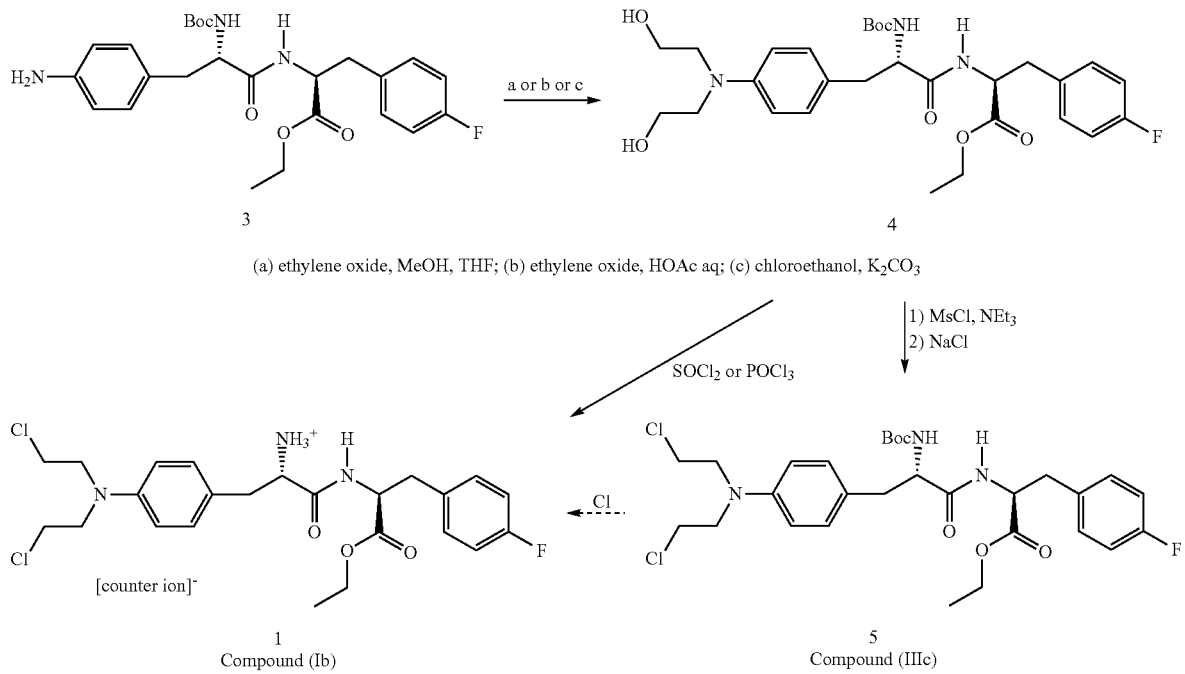

Scheme 2. Alternative pathways to melflufen (a) ethylene oxide, MeOH, THF; (b) ethylene oxide, HOAc aq; (c) chloroethanol, $K_2CO_3$ The inventors have found that using ethylene oxide in THF (route (a) of Scheme 2), no alkylation occurs at 55° C.; increasing the temperature to 60° C. lead to the dialkylated intermediate being formed, but the reaction was very slow. To increase yield and reaction rate the reaction would require high temperatures, but this would cause increased pressure so that the reaction would need be performed in a pressure reactor. Such conditions are likely lead to formation of side products. Similar reaction conditions but using a 50:50 mixture of ethylene oxide and acetic acid (route (b) of Scheme 2) lead to faster reaction times but formation of side products. Using potassium carbonate and chloroethanol (route (c) of Scheme 2) also lead to formation of side product, possibly due to the chloroethanol undergoing partial trans-esterification with the ethyl ester.

The inventors also attempted chlorination of the di-alkylated compound. Chlorination of the bis-(2-hydroxyethyl) compound (4) of Scheme 2 using thionyl chloride in dichloromethane led to significant de-protected side product formation. Chlorination of the bis-(2-hydroxyethyl) compound (4) of Scheme 2 using $POCl_3$ required high temperature and long reaction times. In addition, both thionyl chloride and $POCl_3$ are challenging to handle at large scale due to safety concerns. The inventors also converted the bis-(2-hydroxyethyl) compound (4) of Scheme 2 to the corresponding dimesylate by treatment with methanesulfonyl chloride and triethylamine. The dimesylate was treated then with sodium chloride in DMF at 120° C. However, the crude product of this reaction contained significant side products making this route unsuitable to be used economically at scale.

routes shown in Scheme 2 require multiple steps to form the N, N-bis-chloroethyl amine and use toxic reagents.

The present inventors have discovered an improved process for the production of melflufen (in particular melflufen in the form of its hydrochloride salt), which provides the compound in an excellent yield and with a very high level of purity.

SUMMARY OF THE INVENTION

The present invention provides a process for the production of compound (III) or a deprotected product thereof:

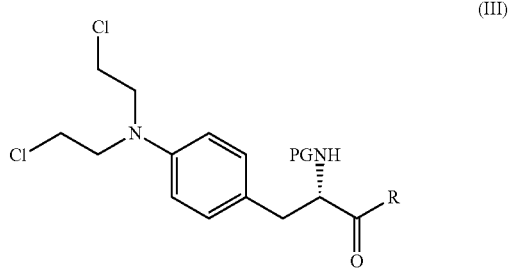

(III)

comprising reacting compound (II)

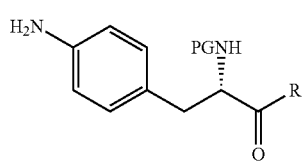

with chloroacetic acid, in the presence of a reducing agent;
wherein PG is a protecting group and R is OH in a suitably protected form or

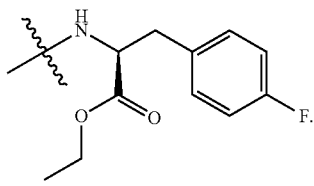 [SMILES: *N[C@@H](Cc1ccc(F)cc1)C(=O)OCC]

It has been surprisingly found by the inventors that conversion of the aromatic amine compound (II) to the nitrogen mustard can be achieved in a single step, with high yield and high purity.

The present invention also provides a process for the production of compound (I), or a salt thereof:

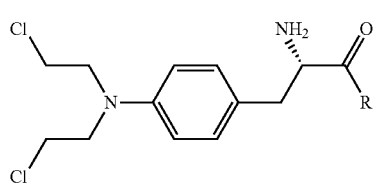

which comprises carrying out the process for the production of compound (III) described above, and further deprotecting compound (III) to produce compound (I), or a salt thereof, wherein is R is OH optionally in a suitably protected form or

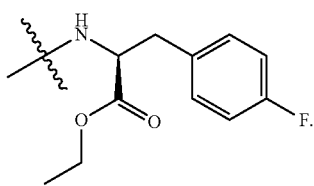 [SMILES: *N[C@@H](Cc1ccc(F)cc1)C(=O)OCC]

The present invention further provides a process for the production of compound (VIb):

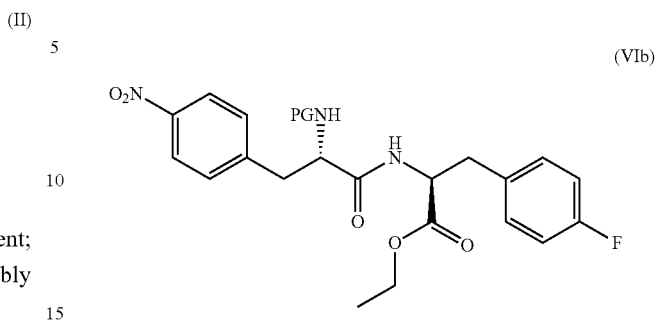

comprising reacting compound (IV):

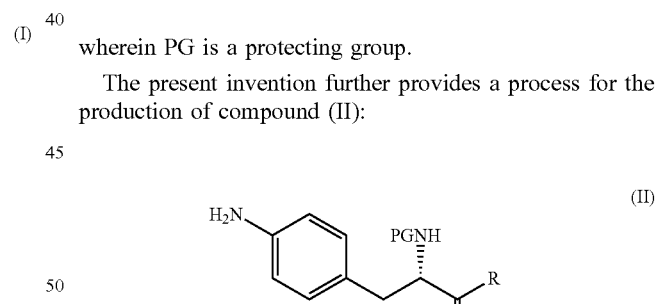

with compound (V):

wherein PG is a protecting group.

The present invention further provides a process for the production of compound (II):

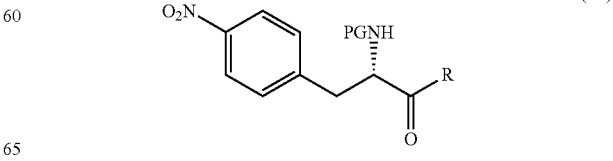

comprising reacting compound (VI):
with a reducing agent, wherein PG is a protecting group and R is OH optionally in a suitably protected form or

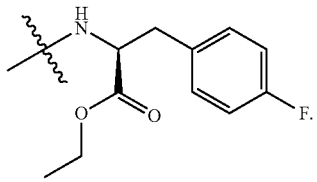 [SMILES: *N[C@@H](Cc1ccc(F)cc1)C(=O)OCC]

The present invention further provides compound having the following structure:

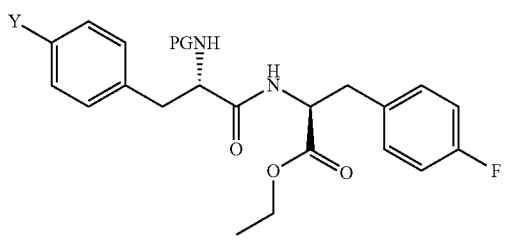

wherein Y is NH$_2$ or NO$_2$, and PG is a protecting group.

DETAILED DESCRIPTION

The present invention provides an improved process for the synthesis of melflufen, or a salt thereof, or melphalan, or a salt thereof, comprising converting an aromatic primary amine (compound (II)) to an aromatic N, N-bis-chloroethyl amine in a single step using chloroacetic acid and a reducing agent. This method works very well and returns good yields of product with high purity. The method is especially efficient because two single steps, bis-hydroxyalkylation and chlorination are replaced by one operation in one vessel.

For the avoidance of doubt, where "melflufen" is referred to herein, unless explicitly stated otherwise, that may refer to melflufen or a salt thereof (for example melflufen hydrochloride).

For the avoidance of doubt, an embodiment or preferred aspect of any one feature of the method of the invention, or compound described herein, may be combined with any embodiment or preferred aspect of another feature of the method of the invention, or compound described herein, to create a further embodiment.

Melphalan has 'L' stereochemistry; melflufen has 'LL' stereochemistry, and it is the 'L' and 'LL' stereochemistry that is in the structures depicted in this application. The methods of the current invention, and the compounds described herein, are equally applicable to the 'D', or 'DL', 'LD' and 'DD' isomers or mixtures (including racemic mixtures) of the isomers.

The present invention provides a process for the production of compound (III), or a deprotected product thereof:

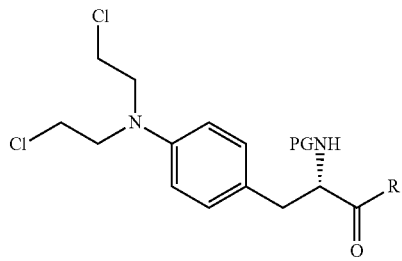

comprising the following step:
(c) reacting compound (II)

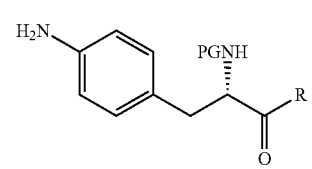

with chloroacetic acid, in the presence of a reducing agent; wherein PG is a protecting group; and R is OH in a suitably protected form or

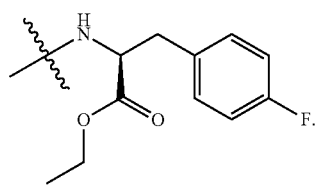 [SMILES: *N[C@@H](Cc1ccc(F)cc1)C(=O)OCC]

In preferred embodiments of the invention, R is

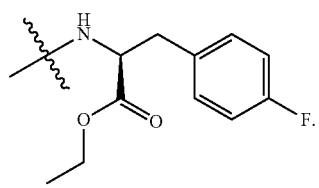

Thus the invention provides a process for the production of compound (IIIb), or a deprotected product thereof:

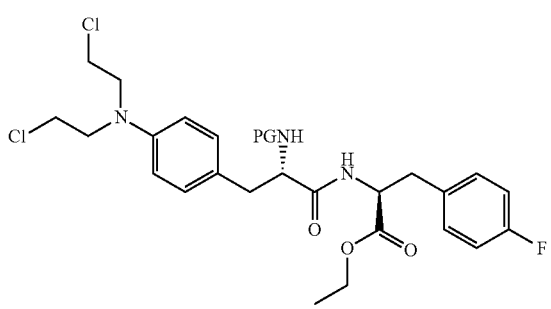

comprising the following step:
(c) reacting compound (IIb)

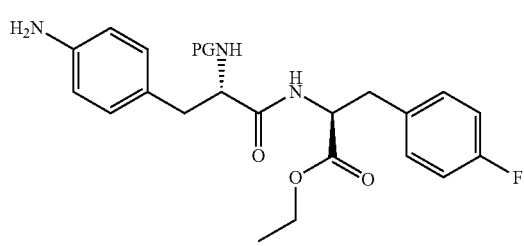

(IIb)

with chloroacetic acid, in the presence of a reducing agent; wherein PG is a protecting group.

PG is a protecting group suitable for protection of a primary amine. Such protecting groups are well known to the skilled man, see for example Wuts, P. G. M., Greene's Protective Groups in Organic Synthesis, 5$^{th}$ Edition (2014) John Wiley & Sons, Inc. Choosing a protecting group is conventional and within the skilled man's normal practice. For example, PG may be selected from the group consisting of methyl oxycarbonyl, ethyl oxycarbonyl, 9-fluorenylmethyl oxycarbonyl (Fmoc), t-butyl oxycarbonyl (Boc), benzyl oxycarbonyl (Cbz), p-methoxybenzyl oxycarbonyl (Moz), 1-adamantyl oxycarbonyl (Adoc), p-bromobenzyl oxycarbonyl, trifluoroacetyl, chloroacetyl, phenylacetyl, benzacetyl, p-toluenesulfonyl (tosyl, Ts), 2-nitrobenzenesulfonyl (Nps), t-butylsulfonyl (Bus), 2- or 4-nitrobenzenesulfonyl (Nosyl), 2,4-dinitronenzesulfonyl (DNs), and 2-naphthalenesulfonyl.

For example, the compound of formula (IIIb) may be: methyl oxycarbonyl-L-melphalan, ethyl oxycarbonyl-L-melphalan, 9-fluorenylmethyl oxycarbonyl-L-melphalan, t-butyl oxycarbonyl-L-melphalan, benzyl oxycarbonyl-L-melphalan, p-methoxybenzyl oxycarbonyl-L-melphalan, 1-adamantyl oxycarbonyl-L-melphalan, p-bromobenzyl oxycarbonyl-L-melphalan, trifluoroacetyl-L-melphalan, chloroacetyl-L-melphalan, phenylacetyl-L-melphalan, benzacetyl-L-melphalan, p-toluenesulfonyl-L-melphalan, 2-nitrobenzenesulfonyl-L-melphalan, t-butylsulfonyl-L-melphalan, 2- or 4-nitrobenzenesulfonyl-L-melphalan, 2,4-dinitronenzesulfonyl-L-melphalan, 2-naphthalenesulfonyl-L-melphalan; methyloxycarbonyl-L-melphalanyl-L-p-fluorophenylalanine ethyl ester, ethyl oxycarbonyl-L-melphalanyl-L-p-fluorophenylalanine ethyl ester, 9-fluorenylmethyl oxycarbonyl-L-melphalanyl-L-p-fluorophenylalanine ethyl ester, t-butyl oxycarbonyl-L-melphalanyl-L-p-fluorophenylalanine ethyl ester, benzyl oxycarbony-L-melphalanyl-L-p-fluorophenylalanine ethyl ester, p-methoxybenzyl oxycarbonyl-L-melphalanyl-L-p-fluorophenylalanine ethyl ester, 1-adamantyl oxycarbonyl-L-melphalanyl-L-p-fluorophenylalanine ethyl ester, p-bromobenzyl oxycarbonyl-L-melphalanyl-L-p-fluorophenylalanine ethyl ester, trifluoroacetyl-L-melphalanyl-L-p-fluorophenylalanine ethyl ester, chloroacetyl-L-melphalanyl-L-p-fluorophenylalanine ethyl ester, phenylacetyl-L-melphalanyl-L-p-fluorophenylalanine ethyl ester, benzacetyl-L-melphalanyl-L-p-fluorophenylalanine ethyl ester, p-toluenesulfonyl-L-melphalanyl-L-p-fluorophenylalanine ethyl ester, 2-nitrobenzenesulfonyl-L-melphalanyl-L-p-fluorophenylalanine ethyl ester, t-butylsulfonyl-L-melphalanyl-L-p-fluorophenylalanine ethyl ester, 2- or 4-nitrobenzenesulfonyl-L-melphalanyl-L-p-fluorophenylalanine ethyl ester, 2,4-dinitronenzesulfonyl-L-melphalanyl-L-p-fluorophenylalanine ethyl ester, or 2-naphthalenesulfonyl-L-melphalanyl-L-p-fluorophenylalanine ethyl ester.

For example, the compound of formula (II) may be: ethyl (2S)-2-[[(2S)-3-(4-aminophenyl)-2-(methyloxycarbonylamino)propanoyl]amino]-3-(4-fluorophenyl)propanoate, ethyl (2S)-2-[[(2S)-3-(4-aminophenyl)-2-(ethyloxycarbonylamino)propanoyl]amino]-3-(4-fluorophenyl)propanoate, ethyl (2S)-2-[[(2S)-3-(4-aminophenyl)-2-(9-fluorenylmethyloxycarbonylamino)propanoyl]amino]-3-(4-fluorophenyl)propanoate, ethyl (2S)-2-[[(2S)-3-(4-aminophenyl)-2-(tert-butoxycarbonylamino)propanoyl]amino]-3-(4-fluorophenyl)propanoate, ethyl (2S)-2-[[(2S)-3-(4-aminophenyl)-2-(benzyloxycarbonylamino)propanoyl]amino]-3-(4-fluorophenyl)propanoate, ethyl (2S)-2-[[(2S)-3-(4-aminophenyl)-2-(p-methoxybenzyloxycarbonylamino)propanoyl]amino]-3-(4-fluorophenyl)propanoate, ethyl (2S)-2-[[(2S)-3-(4-aminophenyl)-2-(1-adamantyloxycarbonylamino)propanoyl]amino]-3-(4-fluorophenyl)propanoate, ethyl (2S)-2-[[(2S)-3-(4-aminophenyl)-2-(p-bromobenzyloxycarbonylamino)propanoyl]amino]-3-(4-fluorophenyl)propanoate, ethyl (2S)-2-[[(2S)-3-(4-aminophenyl)-2-(trifluoroacetylamino)propanoyl]amino]-3-(4-fluorophenyl)propanoate, ethyl (2S)-2-[[(2S)-3-(4-aminophenyl)-2-(chloroacetylamino)propanoyl]amino]-3-(4-fluorophenyl)propanoate, ethyl (2S)-2-[[(2S)-3-(4-aminophenyl)-2-(phenylacetylamino)propanoyl]amino]-3-(4-fluorophenyl)propanoate, ethyl (2S)-2-[[(2S)-3-(4-aminophenyl)-2-(benzacetylamino)propanoyl]amino]-3-(4-fluorophenyl)propanoate, ethyl (2S)-2-[[(2S)-3-(4-aminophenyl)-2-(p-toluenesulfonylamino)propanoyl]amino]-3-(4-fluorophenyl)propanoate, ethyl (2S)-2-[[(2S)-3-(4-aminophenyl)-2-(2-nitrobenzenesulfonylamino)propanoyl]amino]-3-(4-fluorophenyl)propanoate, ethyl (2S)-2-[[(2S)-3-(4-aminophenyl)-2-(t-butylsulfonylamino)propanoyl]amino]-3-(4-fluorophenyl)propanoate, ethyl (2S)-2-[[(2S)-3-(4-aminophenyl)-2-(4-nitrobenzenesulfonylamino)propanoyl]amino]-3-(4-fluorophenyl)propanoate, ethyl (2S)-2-[[(2S)-3-(4-aminophenyl)-2-(2-nitrobenzenesulfonylamino)propanoyl]amino]-3-(4-fluorophenyl)propanoate, ethyl (2S)-2-[[(2S)-3-(4-aminophenyl)-2-(2,4-dinitronenzesulfonylamino)propanoyl]amino]-3-(4-fluorophenyl)propanoate, or ethyl (2S)-2-[[(2S)-3-(4-aminophenyl)-2-(2-naphthalenesulfonyl amino)propanoyl]amino]-3-(4-fluorophenyl)propanoate.

Preferably PG is selected from the group consisting of Fmoc, Boc, Cbz, Moz, Adoc, bromobenzyl carbamate, and trifluoroacetamide. More preferably PG is Boc.

Thus the invention provides a process for the production of compound (IIIa), or a deprotected product thereof:

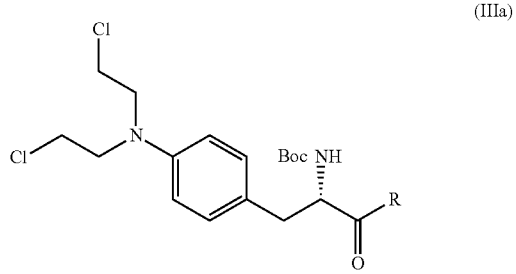

(IIIa)

comprising the following step:
(c) reacting compound (IIa)

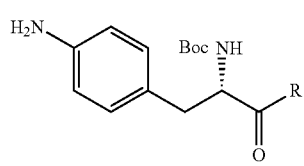
(IIa)

with chloroacetic acid, in the presence of a reducing agent; wherein and R is OH in a suitably protected form or

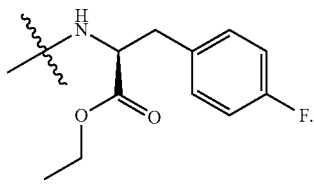 [SMILES: *N[C@@H](Cc1ccc(F)cc1)C(=O)OCC]

In embodiments where R is OH in a suitably protected form, the OH group (and optionally the adjacent carbonyl group) may be protected by any group suitable for protection of a carboxylic acid. Such protecting groups are well known to the skilled man, see for example Wuts, P. G. M., Greene's Protective Groups in Organic Synthesis, 5th Edition (2014) John Wiley & Sons, Inc. Choosing a protecting group for a carboxylic acid is conventional and within the skilled man's normal practice. For example, the protecting group may be selected from the group consisting of methyl ester, methoxymethyl ester, 9-fluorenylmethyl ester, t-butyl ester, benzyl ester, diphenylmethyl ester, triphenylmethyl ester, 2,6-dimethylphenyl ester, tremethylsilyl ester, triethylsilyl ester, 2-(trimethylsilyl)ethoxymethyl ester, 2-(trimethylsilyl)ethyl ester, S-t-butyl ester, and 2-alkyl-1,3-oxazoline.

In an especially preferred embodiment, PG is Boc and R is

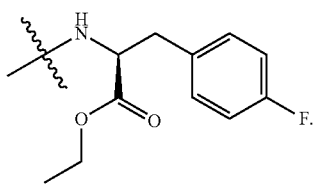 [SMILES: *N[C@@H](Cc1ccc(F)cc1)C(=O)OCC]

Thus the invention provides a process for the production of compound (IIIc), or a deprotected product thereof:

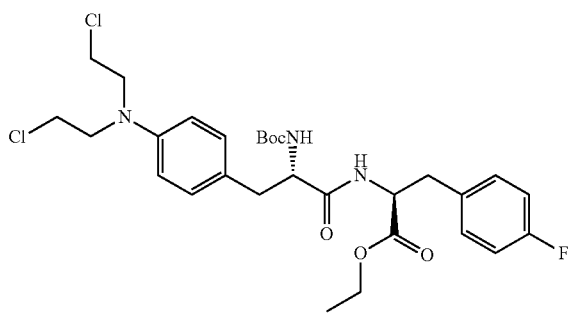
(IIIc)

comprising the following step:
(c) reacting compound (IIc)

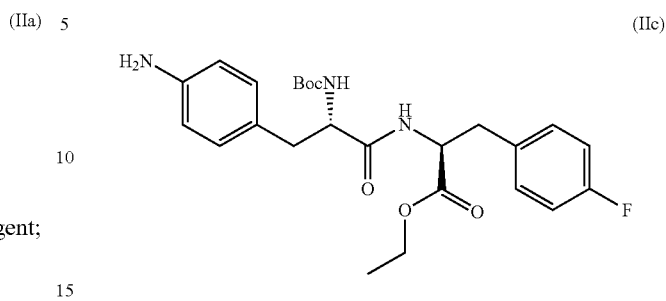
(IIc)

with chloroacetic acid, in the presence of a reducing agent.

The reducing agent for use in step (c) of the present invention may be, for example, a reducing agent suitable for use in a reductive amination or reductive alkylation reaction.

Preferably the reducing agent is a hydride donor, for example a reducing agent selected from the group consisting of a borane, a borane-Lewis base complex, a borohydride, a metal hydride, and $H_2$ in the presence of a metal catalyst. In certain embodiments of the invention the reducing agent is selected from the group consisting of $B_2H_6$, $B_{10}H_{14}$, $BH_3SMe_2$ (borane dimethylsulfide, BMS), $BH_3THF$, $NaBH_4$, $LiBH_4$, $NaBH_3CN$, aluminium hydride (alane), sodium bis(2-methoxyethoxy)aluminium hydride and $H_2$ in the presence of a metal catalyst (for example a catalyst selected from the group consisting of palladium, platinum, nickel, ruthenium, rhodium, and a compound thereof (for example an oxide thereof), optionally on a support, for example carbon). Where the reducing agent is $H_2$ preferably the catalyst is palladium ($H_2$/Pd). More preferably the reducing agent is selected from the group consisting of a borane and a borane-Lewis base complex, for example $B_2H_6$, $B_{10}H_{14}$, $BH_3SMe_2$, BMS or $BH_3THF$. Most preferably the reducing agent is selected from the group consisting of BMS and $BH_3THF$. Even more preferably the reducing agent is BMS.

The reaction is preferably performed in the presence of solvent. Choosing a suitable solvent is conventional and within the normal practice of the skilled man. Preferably the solvent is a polar, aprotic solvent. For example the solvent may be a solvent selected from the group consisting of tetrahydrofuran (THF), 2-methyltetrahydrofuran (2-MeTHF), methyl cyclopentyl ether and dibutyl ether mixtures thereof. More preferably the solvent is selected from the group consisting of THF and 2-MeTHF. In one preferred embodiment the solvent is THF. In another preferred embodiment the solvent is 2-MeTHF.

Preferably the reaction temperature is in the range of from 1 to 80° C. In certain preferred embodiments the reaction temperature is in the range of from 1 to 50, preferably 4 to 45, more preferably 5 to 40° C., for example in the range of from 5 to 30° C. In one preferred embodiment the reaction is carried out in the range of from 5 to 20° C., for example the reaction may be performed starting at 5 to 7° C. and then the temperature increased to around 20 to 30° C., for example around 20° C., during the reaction.

In another preferred embodiment the reaction is carried out in the range of from 1 to 50° C. (more preferably 4 to 45° C.), for example the reaction may be performed starting at around 1 to 10° C. (for example 3 to 7° C., preferably 4 to 6° C.) and then the temperature increased to around 20 to 30° C., for example around 20 to 25° C., during the reaction.

More preferably, the reaction may be performed starting at around 1 to 10° C. (for example 3 to 7° C., preferably 4 to 6° C.) and then the temperature increased to around 5 to 15° C., for example 5 to 13° C., then subsequently to around 20 to 30° C., for example around 20 to 25° C., during the reaction.

In one embodiment, the reaction temperature is initially increased to around 40 to 50° C. For example the reaction temperature is increased to 45° C., then cooled to around 1 to 10° C. (for example 3 to 7° C., e.g. 3, 4, 5, 6, or 7° C., preferably around 4 to 6° C.) and then the temperature increased to around 20 to 30° C., for example around 20 to 25° C., during the reaction. More preferably, the reaction temperature is increased to 45° C., then cooled to around 1 to 10° C. (for example 3 to 7° C., e.g. 3, 4, 5, 6, or 7° C., preferably around 4 to 6° C.) and then the temperature increased to around 5 to 15° C., for example 5 to 13° C., then subsequently to around 20 to 30° C., for example around 20 to 25° C., during the reaction.

Preferably the molar ratio of compound (II):chloroacetic acid is equal to or less than 1:2, preferably equal to or less than 1:5, more preferably equal to or less than 1:10, most preferably equal to or less than 1:20. In certain preferred embodiments, the molar ratio of compound (II):chloroacetic is from 1:2 to 1:100; preferably 1:5 to 1:40; more preferably 1:10 to 1:35; even more preferably 1:15 to 1:30; and most preferably 1:20 to 1:28, for example 1:20, 1:21, 1:22, 1:23, 1:24, 1:25, 1:26, 1:27 or 1:28, preferably 1:26).

Preferably the molar ratio of compound (II):reducing agent is equal to or less than 1:1, preferably equal to or less than 1:3, and more preferably equal to or less than 1:7. In certain preferred embodiments, the molar ratio of compound (II):reducing agent is from 1:1 to 1:50; preferably 1:3 to 1:30; more preferably 1:5 to 1:20; even more preferably 1:8 to 1:18; and most preferably 1:10 to 1:15, for example 1:10, 1:11, 1:12, 1:13, 1:14 or 1:25, preferably 1:13.

The present inventors have further surprisingly found that the reaction of compound (II) to obtain compound (III) as described above is further improved when carried out in the presence of a buffering agent, for example a buffering agent provided by chloroacetate salt which acts as a buffer in combination with the chloroacetic acid. The inventors found that use of a chloroacetate salt as a buffering agent results in compound (III) being obtained in an even higher yield, with higher purity, compared to the process using chloroacetic acid alone. It is observed that there are fewer by-products when the reaction is carried out in the presence of a chloroacetate salt, in particular fewer side products arising from deprotection of the PG group. For example, when compound (II) is compound (IIc), it is observed that there are fewer side products arising from loss of the Boc-group.

In certain preferred embodiments the reaction is performed in the presence of a buffering agent. A buffering agent is one which can act to maintain the pH of a solution near a chosen value after the addition of another acid or base. In the non-aqueous solvent typically used for the reduction of the invention, any compound that can remove acid (i.e. protons) from the solution can be considered to be a buffering agent. For example the buffering agent may be a weak acid or base, in combination with the salt of a weak acid or base, for example phosphoric acid and a phosphate salt, such as sodium phosphate and/or sodium hydrogen phosphate and/or sodium dihydrogen phosphate. As chloroacetic acid is present in the reaction, the buffering agent may be a salt of chloroacetic acid.

In certain particularly preferred embodiments the buffering agent is a chloroacetate salt. The chloroacetate salt may be selected from the group consisting of sodium chloroacetate, potassium chloroacetate, magnesium chloroacetate, calcium chloroacetate and mixtures thereof. Preferably the chloroacetate salt is sodium chloroacetate, i.e. the reaction is performed in the presence of a sodium chloroacetate.

Preferably when the reaction is carried out in the presence of a chloroacetate salt, the amount of chloroacetate salt and chloroacetic acid are such that a buffer solution is obtained. A buffer solution is a solution which resists changes in pH or, in non-aqueous solvents, the amount of acid (i.e. protons) in the solution, when small quantities of an acid or an alkali are added to it.

In embodiments where the reaction is performed in the presence of a chloroacetate salt, the inventors have found that side product formation is minimised by using certain molar ratios of compound (II):chloroacetate salt. Preferably where the reaction is carried out in the presence of a chloroacetate salt, the molar ratio of compound (II):chloroacetate salt is equal to or less than 1:3; more preferably equal to or less than 1:4; and even more preferably equal to or less than 1:7, for example equal to or less than 1:9, equal to or less than 1:12, equal to or less than 1:15. In certain preferred embodiments, the molar ratio of compound (II):chloroacetate salt is from 1:4 to 1:50; preferably 1:5 to 1:30; more preferably 1:7 to 1:20; and even more preferably 1:8 to 1:15, for example 1:10.

In certain preferred embodiments, the molar ratio of chloroacetic acid:chloroacetate salt is at least 1:1, preferably at least 2:1. In certain preferred embodiments, the molar ratio of chloroacetic acid:chloroacetate salt is from 1:1 to 10:1, preferably 1:1 to 6:1; more preferably 2:1 to 5:1; and even more preferably 2:1 to 4:1, for example 2.6:1).

Preferably when the reaction is carried out in the presence of a chloroacetate salt, for every one molar equivalent of compound (I), there are at least 2 molar equivalents of chloroacetic acid, at least 1 molar equivalent of chloroacetate salt; and at least 1 molar equivalent of reducing agent. More preferably, for every one molar equivalent of compound (I), there are at least 8 molar equivalents of chloroacetic acid, at least 4 molar equivalents of chloroacetate salt; and at least 4 molar equivalents of reducing agent. Even more preferably, for every one molar equivalent of compound (I), there are at least 14 molar equivalents of chloroacetic acid, at least 7 molar equivalents of chloroacetate salt; and at least 7 molar equivalents of reducing agent. Even more preferably for every one molar equivalent of compound (I), there are at least 20 molar equivalents of chloroacetic acid, at least 7 molar equivalents of chloroacetate salt; and at least 10 molar equivalents of reducing agent. Most preferably for every one molar equivalent of compound (I), there are at least 24 molar equivalents of chloroacetic acid (for example 24, 26, 28 or 30 molar equivalents), at least 9 molar equivalents of chloroacetate salt (for example 9, 10, 12 or 15 molar equivalents); and at least 12 molar equivalents of reducing agent (for example 12, 13 or 15 molar equivalents).

In certain preferred embodiments, for every one molar equivalent of compound (I), there are from 2 to 60 molar equivalents of chloroacetic acid, from 1 to 50 molar equivalents of chloroacetate salt; and from 1 to 30 molar equivalents of reducing agent. More preferably, there are from 8 to 60 molar equivalents of chloroacetic acid, from 4 to 50 molar equivalents of chloroacetate salt; and from 4 to 30 molar equivalents of reducing agent. Evenore preferably for every one molar equivalent of compound (I), there are from 14 to 40 molar equivalents of chloroacetic acid, from 7 to 25 molar equivalents of chloroacetate salt; and from 7 to 20 molar equivalents of reducing agent; and most preferably for every one molar equivalent of compound (I), there are from 24 to 30 (for example 26) molar equivalents of chloroacetic acid, from 9 to 15 (for example 10) molar equivalents of chloroacetate salt; and from 12 to 15 (for example 13) molar equivalents of reducing agent.

Preferably, once reaction step (c) is complete, the reaction is quenched with a polar, protic solvent, for example an alcohol or water. In one preferred embodiment, the reaction is quenched with ethanol. In another preferred embodiment, the reaction is quenched with water.

In certain preferred embodiments, compound (III) formed according to the present invention is re-crystallised in one or more solvents (for example a solvent selected from ethanol, ethyl acetate, acetone, 2-MeTHF and mixtures thereof) and one or more anti-solvents (for example heptane) to remove impurities. In embodiments where compound (III) is compound (IIIc), the inventors have found that dissolving compound (IIIc) in ethanol, ethyl acetate, acetone or 2-MeTHF at elevated temperatures, lowering the temperature and adding, for example, heptane can increase the purity. For example, recrystallization at 50° C. in approximately seven volumes of acetone, followed by addition of heptane and cooling, can improve the purity of the produce from 96.8 to 98.6 area % by HPLC. In certain embodiments, compound (III) (e.g. compound (IIIc)) is recrystallized in a mixture of acetone/heptane or a mixture of 2-MeTHF/heptane.

In embodiments where the reaction is quenched with water, after the addition of water compound (III) may be precipitated out of the reaction solution (for example by cooling the reaction solution of around 4 to 8° C.) and then re-dissolved in the reaction solution at elevated temperatures (for example around 30 to 40° C.). The organic and aqueous phases may then be separated, and the organic phase washed (for example washed with an aqueous salt solution (e.g. aqueous NaCl, preferably 20% aqueous NaCl)). The organic phase may then be concentrated to precipitate out compound (III). Preferably compound (III) may then washed with solvent, for example an aprotic solvent, or mixture of aprotic solvent, and more preferably a 2-MeTHF/heptane mixture. In embodiments where compound (III) is compound (IIIc), the inventors have found that these isolation steps result in a surprisingly high purity of compound (IIIc) without the need for further purification steps (e.g. re-crystallisation).

A deprotected product of compound (III) or (IIIa) according to the present invention is a compound of formula (III) or (IIIc) wherein the PG protecting group is removed or, when R is OH in a suitably protected form, the OH protecting group is removed. Preferably, the PG protecting group is removed (e.g. a compound of formula (I)). More preferably the PG protecting group is removed and, when R is OH in a suitably protected form, the OH protecting group is removed.

A deprotected product of compound (IIIb) or (IIIc) according to the present invention is a compound of formula (IIIb) or (IIIc) wherein the PG protecting group is removed (e.g. a compound of formula (Ib)).

In certain embodiments of the invention a salt of compound (III) or a salt of a deprotected product of compound (III), is formed. As such, the invention also provides a process for the production of a salt of compound (III) (for example a salt of compound (IIa), (IIIb) or (IIc)), or a salt of a deprotected product of compound (III) (for example a salt of a deprotected product of compound (IIa), (IIb) or (IIIc)), comprising a process for the production of compound (III) (for example (IIIa), (IIIb) or (IIIc)) as described above, and a step of forming the salt, for example a step of forming the hydrochloride salt.

The step of forming a salt of compound (III), or a salt of a deprotected product of compound (III), may be a separate step to the step of forming compound (III) or a deprotected product thereof or the step of forming the salt may be carried out as part of the step of forming compound (III) or a deprotected product thereof.

The process may optionally comprise the further step (d) of removing the PG protecting group of compound (III) to obtain compound (I), or a salt thereof:

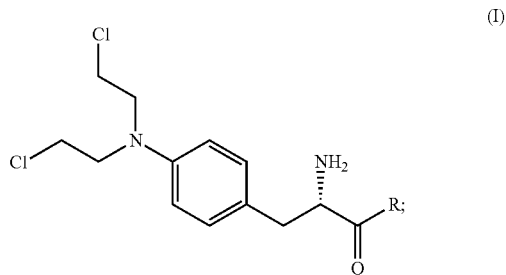

(I)

wherein PG and R are as defined above for step (c).

Preferably, the salt of compound (I) is a pharmaceutically acceptable salt (i.e. salts of compound (I) which are pharmaceutically acceptable are suitable for use in medicine are those wherein a counter-ion is pharmaceutically acceptable). Preferably the salt of compound (I) is a pharmaceutically acceptable acid salt, and more especially a hydrochloride salt.

In particular, suitable salts formed with acids according to the invention include those formed with mineral acids, strong organic carboxylic acids, such as alkanecarboxylic acids of 1 to 4 carbon atoms which are unsubstituted or substituted, for example, by halogen, such as saturated or unsaturated dicarboxylic acids, such as hydroxycarboxylic acids, such as amino acids, or with organic sulfonic acids, such as $(C_1-C_4)$-alkyl- or aryl-sulfonic acids which are unsubstituted or substituted, for example by halogen. Pharmaceutically acceptable acid addition salts include those formed from hydrochloric, hydrobromic, sulphuric, nitric, citric, tartaric, acetic, phosphoric, lactic, pyruvic, acetic, trifluoroacetic, succinic, perchloric, fumaric, maleic, glycolic, lactic, salicylic, oxaloacetic, methanesulfonic, ethanesulfonic, p-toluenesulfonic, formic, benzoic, malonic, naphthalene-2-sulfonic, benzenesulfonic, isethionic, ascorbic, malic, phthalic, aspartic, and glutamic acids, lysine and arginine.

In preferred embodiments of the invention, the salt of compound (I) is obtained. More preferably a pharmaceutically acceptable salt is obtained, and most preferably pharmaceutically acceptable acid salt, and more especially a hydrochloride salt.

In a preferred embodiment R is

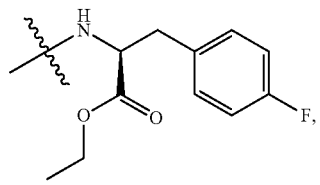 [SMILES: *N[C@@H](Cc1ccc(F)cc1)C(=O)OCC]

and step (d) comprises removing the PG protecting group of compound (IIIb) to obtain compound (Ib) (melflufen), or a salt thereof; wherein PG is as defined above for step (c).

Preferably, the salt of compound (Ib) is obtained. More preferably a pharmaceutically acceptable salt is obtained, most preferably a pharmaceutically acceptable acid salt, and more especially the hydrochloride salt.

A very wide range of reaction conditions may be used to effect the removal of the protecting group PG in step (d). The reaction conditions necessary in step (d) are dependent on the nature of the PG protecting group. Choosing conditions for the removal of a protecting group according to the definition of PG in step (c), above, are conventional and within the normal practice of the skilled man. For example, where the protecting group is a carbamate group, an acid such as hydrochloric acid (HCl) or trifluoroacetic acid (TFA) (preferably HCl) may be used to remove the protecting group. Suitable conditions for removing protecting groups are taught in, for example, Wuts, P. G. M., Greene's Protective Groups in Organic Synthesis, 5$^{th}$ Edition (2014) John Wiley & Sons, Inc.

For example, where PG is Boc (i.e. compound (III) is compound (IIIa)), step (d) comprises reacting compound (IIIa) under acidic reaction conditions, to obtain compound (I) (melflufen or melphalan) or a salt thereof (preferably the hydrochloride salt thereof); wherein PG and R are as defined above for step (c).

In another preferred embodiment PG is Boc and R is

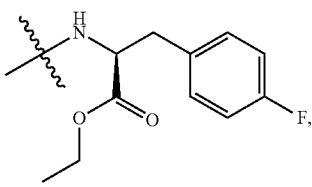

and step (d) comprises removing the PG protecting group of compound (IIIc) to obtain compound (Ib) (melflufen), or a salt thereof. Preferably, a salt of compound (Ib) is obtained. More preferably a pharmaceutically acceptable salt of compound (Ib) is obtained, most preferably a pharmaceutically acceptable acid salt of compound (Ib), and more especially the hydrochloride salt of compound (Ib):

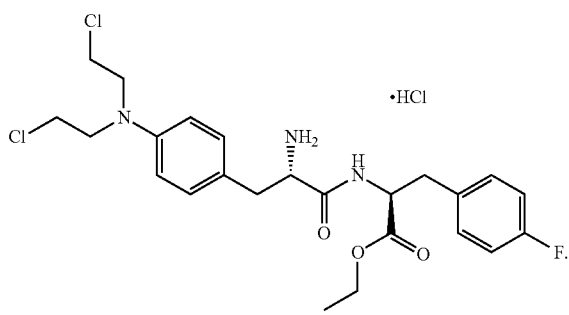 [SMILES: CCOC(=O)[C@H](Cc1ccc(F)cc1)NC(=O)[C@@H](N)Cc1ccc(N(CCCl)CCCl)cc1 ; Cl]

In embodiments wherein PG is an acid labile protecting group, for example Boc, preferably the compound (III) (for example compound (IIIa) or (IIIc)) is reacted under acidic reaction conditions, preferably with HCl, to remove the protecting group, to form compound (I) (for example (Ib)), or a salt thereof. Preferably, the hydrochloride salt of compound (I) (for example (Ib)) is formed.

Examples of a suitable HCl source for step (d) include 1.3 M HCl/EtOH, 2.5 M HCl/EtOH, 1 M HCL/EtOAc, 3 M HCl/EtOH, and 5-6 M HCl/iPrOH. Preferably the molar ratio of compound (III):HCl is from 1:1: to 1:50; more preferably it is from 1:3 to 1:30; even more preferably 1:5 to 1:20; most preferably 1:7 to 1:17, for example 1:10.

Preferably the solvent for the deprotection is selected from the group consisting of ethanol (EtOH), isopropyl alcohol, ethyl acetate, THF, acetone, and mixtures thereof. For example the reaction may be carried out in a mixture of HCl/EtOH, ethyl acetate/HCl/EtOH, acetone/HCl/EtOH, or THF/HCl/EtOH. For example, HCl/EtOH, acetone/HCl/EtOH, or THF/HCl/EtOH. Preferably the reaction is carried out in a mixture of HCl/EtOH or ethyl acetate/HCl/EtOH.

The product of step (d) may be purified, for example purified by washing with solvent (for example one or more washing with ethanol, for example 3 washings with ethanol) and/or crystallisation (for example recrystallization in ethanol and/or recrystallization in methyl tert-butyl ether; for example recrystallization in methyl tert-butyl ether; or for example recrystallization in methyl tert-butyl ether followed by recrystallization in ethanol).

Preferably, deprotection is a separate step after step (c) in which the N, N-bis-chloroethyl amine is formed. However, in certain embodiments, deprotection can be carried out as part of step (c) in a one-pot synthesis. In that case, the process of the invention provides the deprotected product, compound (I), directly.

In certain embodiments of the invention a salt of compound (I) (for example a salt of compound (Ib)) is formed. As such, the invention also provides a process for the production of a salt of compound (I) (for example a salt of compound (Ib)), comprising a process for the production of compound (I) (for example (Ib)) as described above, and a step of forming a salt of compound (I) (for example a salt of compound (Ib)), for example a step of forming the hydrochloride salt.

The step of forming a salt of compound (I) (for example a salt of compound (Ib)) may be a separate step after the deprotection step (d), or the step of forming the salt may be carried out as part of the deprotection step (d). In one preferred embodiment, the step of forming the salt of compound (I) (for example the salt of compound (Ib), preferably the hydrochloride salt of compound (Ib)) is carried out as part of the deprotection step (d). In such an embodiment, preferably PG is an acid labile protecting group, for example Boc; and preferably the compound (III) (for example compound (IIIa) or (IIIc)) is reacted under acidic reaction conditions, and more preferably with HCl, to remove the protecting group to form compound (I) (for example (Ib)) in salt thereof. More preferably, the hydrochloride salt of compound (I) (for example (Ib)) is formed.

In another embodiment, the step of forming a salt of compound (I) (for example a salt of compound (Ib)) and the step of deprotection may be carried out as part of step (c) in a one-pot synthesis. In that case, the process of the invention provides the salt of the deprotected product, compound (I), directly.

The present inventors have additionally discovered a novel process comprising reacting two substituted phenylalanines: PG-p-nitro-L-phenylalanine (compound (IV)) and p-fluoro-L-phenylalanine ethyl ester (compound (V)), wherein PG is as defined for step (c), above, to produce compound (VIb):

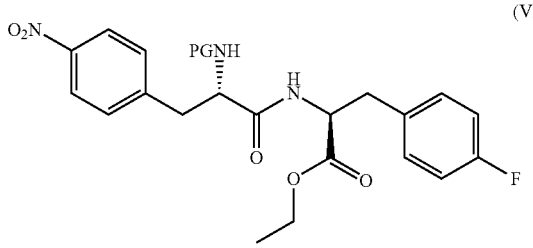

(VIb)

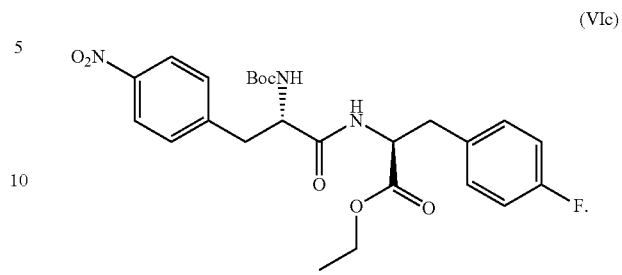

(VIc)

The amino acids are coupled to form compound (VIb). Compound (VIb) may then be reduced to form the aromatic amine compound (IIb). The process to form compound (IIb) uses non-toxic starting materials, and thus when used in a process for synthesising melflufen, avoids the production of toxic products before the final steps. As such, this process is much safer than using a bis-(2-chloroethyl) containing starting material, as used in the known process for the synthesis of melflufen.

Thus the present invention also provides a process for the production of compound (VIb) comprising the following step:

(a) reacting compound (IV):

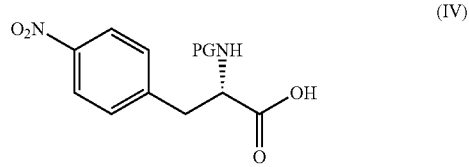

(IV)

with compound (V):

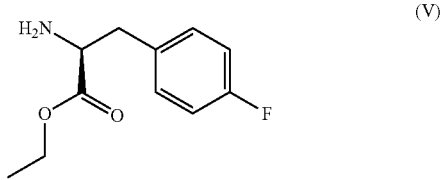

(V)

wherein PG is as defined above for step (c).

In certain preferred embodiments, PG is Boc, and the process comprises the following step:

(a) reacting compound (IVc):

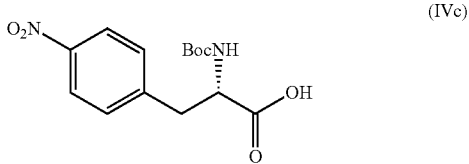 [SMILES: CC(C)(C)OC(=O)N[C@@H](Cc1ccc([N+](=O)[O-])cc1)C(=O)O]

(IVc)

with compound (V) to obtain compound (VIc):

Step (a) of the process of the invention may be carried out under any conditions suitable for an amide coupling reaction. Choosing amide coupling reaction conditions is conventional and within the normal practice of the skilled man. The reaction conditions necessary may depend on the nature of the PG protecting group.

Amide coupling reagents suitable for use in the present invention include: carbodiimides, for example dicyclohexylcarbodiimide (DCC), diisopropylcarbodiimide (DIC), ethyl-(N',N'-dimethylamino)propylcarbodiimide hydrochloride (EDC); phosphonium-based reagents, for example (benzotriazol-1-yloxy)tris(dimethylamino)phosphonium hexafluorophosphate (BOP), benzotriazol-1-yl-oxytripyrrolidinophosphonium hexafluorophosphate (PyBOP); aminium-based reagents, for example N,N,N',N'-tetramethyl-O-(1H-benzotriazol-1-yl)uronium hexafluorophosphate (HBTU), 1-[Bis(dimethylamino)methylene]-1H-1,2,3-triazolo[4,5-b]pyridinium 3-oxid hexafluorophosphate (HATU), O-(benzotriazol-1-yl)-N,N,N',N'-tetramethyluronium tetrafluoroborate (TBTU), O-(6-chlorobenzotriazol-1-yl)-N,N,N',N'-tetramethyluronium hexafluorophosphate (HCTU), O-(3,4-dihydro-4-oxo-1,2,3-benzotriazine-3-yl)-N,N,N',N'-tetramethyluronium tetrafluoroborate (TDBTU); immonium aminium-based reagents, for example (1H-benzotriazol-1-yloxy)-N,N-dimethylmethaniminium hexachloroantimonate (BOMI), 5-(1H-benzotriazol-1-yloxy)-3,4-dihydro-1-methyl 2H-pyrrolium hexachloroantimonate (BDMP) and 5-(7-azabenzotriazol-1-yloxy)-3,4-dihydro-1-methyl 2H-pyrrolium hexachloroantimonate (AOMP); agents generating acids chlorides, for example thionyl chloride, phosphorus pentachloride, triphosgene, triazines (e.g. cyanuric chlorides, cyanuric fluoride, and derivatives thereof), tetramethylfluoroformamidinium hexafluorophosphate (TFFH), bis(tetramethylene)fluoroformamidinium (BTFFH), and 1,3-dimethyl-2-fluoro-4,5-dihydro-1H-imidazolium hexafluorophosphate (DFIH); or other coupling reagents, for example 3-(diethylphosphoryloxy)-1,2,3-benzotriazin-4(3H)-one (DEPBT), carbonyldilmidazole (CDI), propylphosphonic anhydride (T3P), and N-Ethoxycarbonyl-2-ethoxy-1,2-dihydroquino line (EEDQ).

A further agent may be included in the amide coupling conditions to suppress racemization, for example hydroxybenzotriazole (HOBt), 1-hydroxy-7-azabenzotriazole (HOAt), ethyl 2-cyano-2-(hydroxyimino)acetate (oxyma). Preferably, the further agent to suppress racemization is HOBt.

In certain preferred embodiments, the amide coupling is performed using HATU or HBTU with N,N-Diisopropylethylamine (DIPEA) or N-methylmorpholine (NMM); using EDC and Hydroxybenzotriazole (HOBt) with DIPEA or NMM; using propylphosphonic anhydride (T3P) with DIPEA; or using PyBOP with DIPEA.

Preferably, step (a) is performed in the presence of EDC. More preferably step (a) is performed in the presence of EDC, HOBt and NMM. Using these reaction conditions, compound (VIb) may be obtained with a very high crude purity, for example over 96% purity. Most preferably, step (a) is performed in the presence of 1.1 equivalents of EDC, 0.1 equivalents of HOBt, 3.5 equivalents of NMM, and using approximately 1 equivalent of each of compound (IV) and compound (V).

Choosing a solvent for the specific amide coupling reaction conditions is conventional and within the normal practice of the skilled man. Preferably the solvent for the reaction is an aprotic solvent. For example, the solvent may be one selected from the group consisting of ethyl acetate, acetone, THF, 2-MeTHF, dichloromethane, dimethylformamide; cyclopentyl methyl ester and mixtures thereof. Preferably the solvent is selected from the group consisting of DMF, ethyl acetate, acetone, 2-MeTHF and mixtures thereof. More preferably it is ethyl acetate or acetone. The present inventors have found that acetone is a surprisingly effective solvent for the amide coupling reaction of the invention, keeping the reaction mixture as a solution throughout the reaction. As such, most preferably the solvent is acetone.

The product of step (a) may be purified further before the next reaction step, for example purified by crystallisation. Alternatively, the product of step (a), may be used directly in process step (b) (described below) without further isolation or purification of compound (VIb).

Purity of the product in each step from (a) to (d) of the reaction has been found to be of importance, as impurities in each step can carry through the process, for example the purity of the product of step (a) has an effect on the purity of the subsequent reaction steps (b), (c) and (d). Therefore, it is of importance that each step in the process leads to a product with as high a purity as possible, to obtain the highest purity of compound (III) and hence compound (I). Each of steps (a) to (d) of the present invention results in products with high purity, making the overall reaction process particularly effective for making compound (III), and hence compound (I), having high purity.

The present invention also provides a process of the invention for the production of compound (II) comprising the following step:
(b) reacting compound (VI)

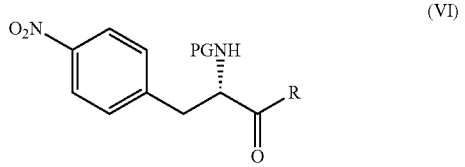

with a reducing agent,
wherein PG is as defined above for step (c) and R is OH optionally in a suitably protected form or

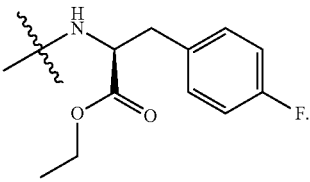 [SMILES: *N[C@@H](Cc1ccc(F)cc1)C(=O)OCC]

For example, the compound of formula (VI) may be: ethyl (2S)-2-[[(2S)-3-(4-nitrophenyl)-2-(methyloxycarbonylamino)propanoyl]amino]-3-(4-fluorophenyl)propanoate, ethyl (2S)-2-[[(2S)-3-(4-nitrophenyl)-2-(ethyloxycarbonylamino)propanoyl]amino]-3-(4-fluorophenyl)propanoate, ethyl (2S)-2-[[(2S)-3-(4-nitrophenyl)-2-(9-fluorenylmethyloxycarbonylamino)propanoyl]amino]-3-(4-fluorophenyl) propanoate, ethyl (2S)-2-[[(2S)-3-(4-nitrophenyl)-2-(tert-butoxycarbonylamino)propanoyl]amino]-3-(4-fluorophenyl)propanoate, ethyl (2S)-2-[[(2S)-3-(4-nitrophenyl)-2-(benzyloxycarbonylamino)propanoyl] amino]-3-(4-fluorophenyl)propanoate, ethyl (2S)-2-[[(2S)-3-(4-nitrophenyl)-2-(p-methoxybenzyloxycarbonylamino) propanoyl]amino]-3-(4-fluorophenyl)propanoate, ethyl (2S)-2-[[(2S)-3-(4-nitrophenyl)-2-(1-adamantyloxycarbonylamino)propanoyl]amino]-3-(4-fluorophenyl)propanoate, ethyl (2S)-2-[[(2S)-3-(4-nitrophenyl)-2-(p-bromobenzyloxycarbonylamino)propanoyl]amino]-3-(4-fluorophenyl) propanoate, ethyl (2S)-2-[[(2S)-3-(4-nitrophenyl)-2-(trifluoroacetylamino)propanoyl]amino]-3-(4-fluorophenyl) propanoate, ethyl (2S)-2-[[(2S)-3-(4-nitrophenyl)-2-(chloroacetylamino)propanoyl]amino]-3-(4-fluorophenyl) propanoate, ethyl (2S)-2-[[(2S)-3-(4-nitrophenyl)-2-(phenylacetylamino)propanoyl]amino]-3-(4-fluorophenyl) propanoate, ethyl (2S)-2-[[(2S)-3-(4-nitrophenyl)-2-(benzacetylamino)propanoyl]amino]-3-(4-fluorophenyl) propanoate, ethyl (2S)-2-[[(2S)-3-(4-nitrophenyl)-2-(p-toluenesulfonylamino)propanoyl]amino]-3-(4-fluorophenyl)propanoate, ethyl (2S)-2-[[(2S)-3-(4-nitrophenyl)-2-(2-nitrobenzenesulfonylamino)propanoyl] amino]-3-(4-fluorophenyl)propanoate, ethyl (2S)-2-[[(2S)-3-(4-nitrophenyl)-2-(t-butylsulfonylamino)propanoyl] amino]-3-(4-fluorophenyl)propanoate, ethyl (2S)-2-[[(2S)-3-(4-nitrophenyl)-2-(4-nitrobenzenesulfonylamino) propanoyl]amino]-3-(4-fluorophenyl)propanoate, ethyl (2S)-2-[[(2S)-3-(4-nitrophenyl)-2-(2-nitrobenzenesulfonylamino)propanoyl]amino]-3-(4-fluorophenyl)propanoate, ethyl (2S)-2-[[(2S)-3-(4-nitrophenyl)-2-(2,4-dinitronenzesulfonylamino)propanoyl]amino]-3-(4-fluorophenyl)propanoate, or ethyl (2S)-2-[[(2S)-3-(4-nitrophenyl)-2-(2-naphthalenesulfonyl amino)propanoyl]amino]-3-(4-fluorophenyl)propanoate.

For example, where PG is Boc, the process may comprise the step:
(b) reacting compound (VIa):

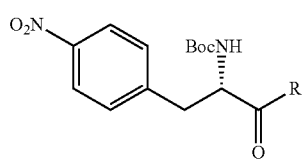

with a reducing agent, for example $H_2$/Pd/C,
to obtain compound (IIIa), wherein R is OH optionally in a suitably protected form or

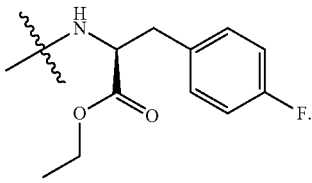 [SMILES: *N[C@@H](Cc1ccc(F)cc1)C(=O)OCC]

In certain preferred embodiments where R is

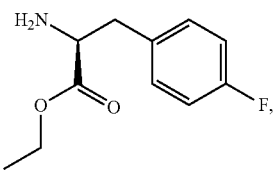

the process may comprise the step:
(b) reacting compound (VIb) with a reducing agent, for example H$_2$/Pd/C, to obtain compound (IIb)
wherein PG is as defined in step (c) above.

In certain preferred embodiments where PG is Boc and R is

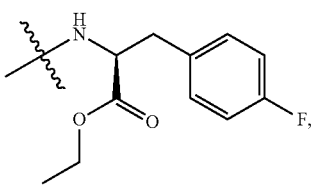

the process may comprise the step:
(b) reacting compound (VIc) with a reducing agent, for example H$_2$/Pd/C, to obtain compound (IIc).

Step (b) of the process of the invention may be carried out under conditions suitable for reducing a nitro group to an amine group. The reaction conditions necessary may be dependent on the nature of the PG protecting group. Choosing reduction reaction conditions is conventional and within the normal practice of the skilled man.

In certain preferred embodiments, the reduction reaction of step (b) may be a hydrogenation reaction, more preferably a catalytic hydrogenation reaction, i.e. the hydrogenation reaction is carried out in the presence of a hydrogen and a catalyst. Therefore, the reducing agent of step (b) may be hydrogen (H$_2$) and a catalyst. Preferably, the catalyst is a metal catalyst, for example a catalyst selected from the group consisting of platinum, palladium, rhodium, ruthenium, nickel (for example Raney nickel or Urushibara nickel), iron, and a compound thereof (for example an oxide thereof). The catalyst may be homogeneous or heterogeneous; preferably it is heterogeneous. Preferably the catalyst is on a catalyst support, for example a catalyst support selected from the group consisting of carbon, alumina, silica and calcium carbonate. Most preferably the catalyst support is carbon.

In a preferred embodiment of the invention, the catalyst is palladium (Pd), and more preferably palladium on carbon (Pd/C), i.e. the reduction reaction (b) uses H$_2$ gas with Pd/C catalyst (H$_2$/Pd/C) (i.e. the reducing agent of step (b) is H$_2$/Pd/C). More preferably, the Pd/C catalyst is 1 to 15% Pd on activated carbon, preferably 1 to 10% Pd on activated carbon, more preferably 3 to 6% Pd on activated carbon, most preferably 3 to 5% Pd on activated carbon. Preferably the Pd/C catalyst is an approximately 50% moist catalyst.

Preferably, the H$_2$ pressure is from 1 to 8 bar, more preferably from 1 to 3 bar. The catalyst is preferably present from 1 to 30 w/w %, more preferably from 3 to 20 w/w %; even more preferably from 3 to 10 w/w %, and most preferably from 3 to 6 w/w %, for example 3, 4, 4.5, 5 or 6 w/w %.

Choosing a solvent for the hydrogenation reaction is conventional and within the normal practice of the skilled man. Examples of suitable solvents include 2-MeTHF, ethyl acetate, ethanol and mixtures thereof. Preferably the solvent is 2-MeTHF.

After completion, the catalyst may be removed by filtration, for example by filtration through a carbon frit.

The product of step (b) (compound (II)) may be crystallized in one or more solvents (for example ethanol, ethyl acetate, 2-MeTHF and mixtures thereof) and one or more anti-solvents (for example heptane) to remove impurities before use in step (c) of the process. The inventors have found that dissolving compound (II) in, for example, ethanol, ethyl acetate, or 2-MeTHF, or mixtures thereof, at elevated temperatures, lowering the temperature and adding, for example, heptane increases the purity. Preferably compound (II) is crystallized from a 2-MeTHF/heptane mixture.

Step (b) as described above may be used in combination with steps (c) and/or (d) described above. Thus the present invention provides a process comprising one or more of the following steps:
(b) A process for the production of compound (II) comprising reacting compound (VI) with a reducing agent;
(c) A process for the production of compound (III), or a deprotected product thereof, or a salt of a deprotected product thereof, comprising reacting compound (II) with chloroacetic acid, in the presence of a reducing agent; and/or
(d) A process for the production of compound (I), or a salt thereof, comprising deprotecting compound (III) to produce compound (I) or a salt thereof;
wherein PG is a protecting group and R is OH optionally in a suitably protected form or

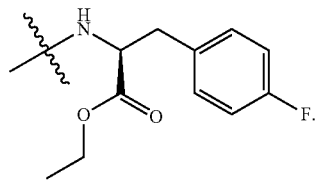 [SMILES: *N[C@@H](Cc1ccc(F)cc1)C(=O)OCC]

Preferably PG is Boc.

In one preferred embodiment, step (c) is a process for the production of a deprotected product of compound (III), and the process further comprises a step of forming a salt of the deprotected product of compound (III). In another preferred embodiment, step (d) is a process for the production of a salt of compound (I), and the process further comprises a step of forming a salt of the compound (I).

In one preferred embodiments where R is

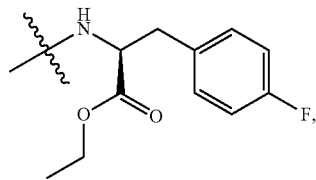 [SMILES: *N[C@@H](Cc1ccc(F)cc1)C(=O)OCC]

steps (a) and/or (b) as described above may be used in combination with steps (c) and/or (d) described above. Thus the present invention provides a process comprising one or more of the following steps (a) a process for the production of compound (VIb) comprising reacting compound (IV) with compound (V); and/or
(b) A process for the production of compound (IIb) comprising reacting compound (VIb) with a reducing agent; and/or
(c) A process for the production of compound (IIIb), or a deprotected product thereof, comprising reacting compound (IIb) with chloroacetic acid, in the presence of a reducing agent; and/or
(d) A process for the production of compound (Ib), or a salt thereof, comprising deprotecting compound (IIIb) to produce compound (Ib) or a salt thereof,
wherein PG is as defined above for step (c).

In such an embodiment, preferably PG is Boc.

In one preferred embodiment, step (c) is a process for the production of a deprotected product of compound (IIIb), and the process further comprises a step of forming a salt of the deprotected product of compound (IIIb). In another preferred embodiment, step (d) is a process for the production of a salt of compound (Ib), and the process further comprises a step of forming a salt of the compound (Ib).

The invention also provides compound (III), (IIIa), (IIIb), (IIIc) or a deprotected product thereof, or a salt of a deprotected product thereof, made by a process described herein; a compound of formula (I), (Ib), or a salt thereof, made by a process described herein; a compound of formula (VIb) made by a process described herein; or a compound of formula (II) or (IIc) made by a process described herein.

Also disclosed herein is a process for the production of compound (X), or a salt thereof, optionally in a suitably protected from:

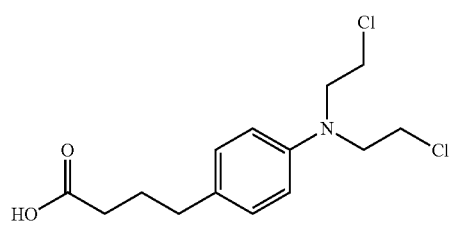

(X)

comprising the following step:
(c) reacting compound (XI)

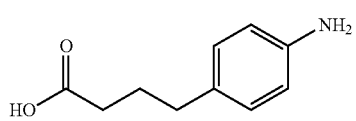

(XI)

with chloroacetic acid, in the presence of a reducing agent and optionally in a suitable solvent.

The preferred reaction conditions are those preferred for step (c) described above.

EXAMPLES

General Experimental Details

Unless stated otherwise, all reagents/solvents were purchased from commercial sources and used without further purification.

Compounds were purified on a HPLC system equipped with a C18 reverse phase column, and using UV detection at wave length 262 nm. All compounds were separated over a gradient of acetonitrile in water.

Example 1—Synthesis of Compound (VIc)

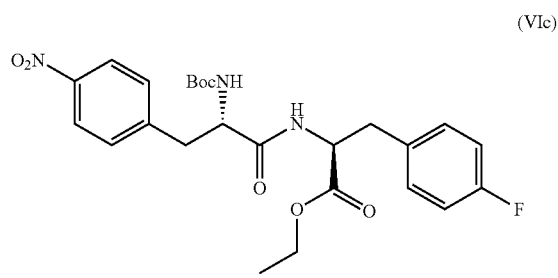 [SMILES: CCOC(=O)[C@H](Cc1ccc(F)cc1)NC(=O)[C@H](Cc1ccc([N+](=O)[O-])cc1)NC(=O)OC(C)(C)C]

(VIc)

To a reactor with overhead stirring, equipped with nitrogen inlet and reflux condenser, was charged Boc-nitrophenylalanine (compound (IVc)) (35.0 g, 112.8 mmol, 1 eq.), followed by acetone (420 mL), N-methylmorpholine (43.4 mL, 394.8 mmol, 3.5 eq.), fluoro-L-phenylalanine ethyl ester hydrochloride (compound (V)) (28.5 g, 115 mmol, 1.02 eq.), EDC (23.8 g, 124.1 mmol, 1.1 eq.) and HOBt.H$_2$O (1.7 g, 11.3 mmol, 0.1 eq.). The slurry was stirred at room temperature for 18.5 h which led to full consumption of compound (IVc) according to HPLC. Water (180 mL) and 2-MeTHF (965 mL) were charged. Approximately 640 g solvent was then removed by evaporation (T$_j$: 35° C.) from the clear two phase orange mixture. 360 mL 2-MeTHF was then added and evaporated off twice. The water phase was acidified to pH 3 via addition of 58 mL 2 M sulfuric acid. The organic layer was heated to 35-40° C. and was then sequentially washed with water (90 mL), twice with saturated aqueous NaHCO$_3$ solution (90 mL) and then brine (90 mL) and finally water (90 mL). To the 2-MeTHF dissolved product was added heptane (270 mL) drop wise at 35-40° C. before the mixture was allowed to reach room temperature overnight with stirring. Another 135 mL heptane was added drop wise before the beige slurry was cooled to 10° C. The product was isolated and was rinsed with 100 mL cold 2-MeTHF/heptane 6/4. Product compound (VIc) was stored moist (82.5 g). A small sample of the product was analyzed by limit of detection (LOD) which revealed the solid to contain 43.8% solvent residues. Based on this, the purified product was obtained in a yield of 82%. The purity was determined by HPLC to be: 99.4 area %.

$^1$H-NMR (300 MHz, DMSO-D$_6$) δ 8.48 (broad d, 1H, J=7.5 Hz), 8.16 (2H, d, J=8.7 Hz), 7.55 (2H, d, J=9 Hz), 7.28 (2H, dd, J=8.7, 8.1 Hz), 7.12-7.02 (3H, m), 4.49 (1H, dd, J=14.4, 7.2 Hz), 4.32-4.24 (1H, m), 4.04 (2H, dd, J=14.4, 7.2 Hz), 3.08-2.95 (3H, m), 2.84 (1H, dd, J=13.2, 10.8 Hz), 1.27 (s, 9H), 1.11 (3H, t, J=7.2 Hz)

$^{13}$C-NMR (75 MHz, DMSO-D$_6$) δ 171.4 (C=O), 171.2 (C=O), 161.2 (C—F, d, J=242.3 Hz), 155.2 (C=O), 146.6 (C), 146.2 (C), 133.1 (C), 131.1 (2 carbon, CH, d, J=8.3 Hz), 130.6 (2 carbon, CH), 123.1 (C), 114.9 (2 carbon, CH, J=20.4 Hz), 78.1 (C), 60.6 (CH$_2$), 55.1 (CH), 53.6 (CH), 37.3 (CH$_2$), 35.9 (CH$_2$), 28.0 (3 carbons, CH$_3$), 14.0 (CH$_3$)

Example 2—Synthesis of Compound (IIc)

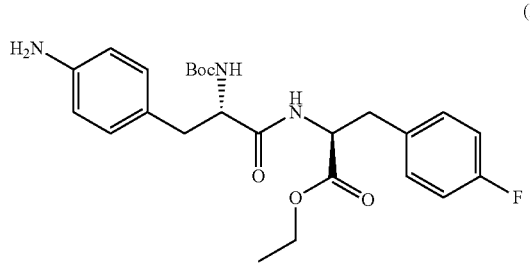

To a hydrogenation autoclave was added wet solid product compound (VIc) (approximately 4.9 g dry weight, 9.7 mmol, 1 eq.), 2-MeTHF (75 mL) and 3 w/w % of a 5% Pd/C-catalyst (147 mg, 50% moist). The reaction mixture was degased with nitrogen and then 1 barg hydrogen gas was charged. Stirring was set to 600 rpm and $T_J$ to 36° C. The reaction was completed in four hours, The hydrogenation autoclave was rinsed with 10 mL 2-MeTHF and the rinsing portion was added to the reaction solution in the E-flask. Charcoal (250 mg, 5 wt %) was then added and the resulting mixture was stirred for 15 minutes at room temperature before it was filtered. The filter was rinsed with 10 mL 2-MeTHF and the rinsing portion was added to the filter. The light yellow/pink filtrate contained white precipitated product. The slurry was heated to approximately 40° C. to dissolve the solid before heptane (42 mL) was added drop wise during one hour. The heating was turned off and the mixture was allowed to reach room temperature with overnight stirring. Additional 21 mL heptane was the added before the mixture was cooled to approximately 7° C. (ice/water bath). The solid was isolated and was washed through with 10 mL cold 2-MeTHF/heptane 6/4. The moist solid (5.7 g) was vacuum dried at 35° C. overnight which gave a dry weight of compound (IIc) of 4.2 g which corresponds to a yield of 91%. The purity was determined by HPLC to be 99.1 area %.

$^1$H-NMR (300 MHz, DMSO-D$_6$) δ 8.26 (1H, d, J=7.5 Hz), 7.26 (dd, 2H, J=8.1, 5.7 Hz), 7.09 (2H, t, J=8.7 Hz), 6.86 (2H, d, J=8.1 Hz), 6.71 (1H, d, J=8.7 Hz), 6.45 (1H, d, J=8.1 Hz), 4.87 (2H, s), 4.45 (1H, dd, J=14.4, 7.5 Hz), 4.07-4.00 (3H, m), 3.06-2.91 (2H, m), 2.71 (1H, dd, J=13.8, 3.9 Hz), 2.54-2.46 (1H, m), 1.31 (s, 9H), 1.11 (3H, t, J=6.9 Hz).

$^{13}$C-NMR (75 MHz, DMSO-D$_6$) δ 171.4 (C=O), 171.2 (C=O), 161.2 (C—F, d, J=242.3 Hz), 155.1 (C=O), 146.9 (C), 133.2 (C, d, J=3.0 Hz), 131.1 (2 carbon, CH, d, J=8.3 Hz), 129.5 (2 carbon, CH), 124.8 (C), 114.8 (2 carbon, CH, J=21.1 Hz), 113.6 (2 carbon, CH), 77.9 (C), 60.5 (CH$_2$), 56.0 (CH), 53.5 (CH), 36.7 (CH$_2$), 35.9 (CH$_2$), 28.1 (3 carbons, CH$_3$), 13.9 (CH$_3$)

The present inventors have repeated Example 2 several times using crude compound (VIc) or recrystallised compound (VIc) (purity: 99.1 area %) as starting material and varying various reaction conditions, e.g. pressure of H$_2$, w/w % of Pd/C, solvent and temperature. The crude purity (97.2 area %) was a slightly higher when recrystallized compound (VIc) was used as starting material than when using crude compound (VIc), in which case the crude purity is generally 95-96 area %. Final yield and purity is also slightly higher than when starting from crude compound (VIc) (98-98.5 area %).

The present inventors have also repeated Example 2 several times varying the Pd/C w/w %, temperature, pressure of H$_2$ and concentration using 2-MeTHF as the solvent. A high conversion of Compound (VIc) (>99.5 area %) was achieved for Pd/C w/w % from 3 to 6 bar; temperature ranges from 30 to 40° C., H$_2$ pressure from 1 to 6 barg, and for varying reaction concentrations. The resulting crude purity was similar in all attempts (95.3-96.2 area %), as was the purity of the isolated product after crystallization from 2-MeTHF/heptane (98.0-98.5 area %).

Example 3—Preparation of Compound (IIIc)

(i) Carried Out Using BH$_3$SMe$_2$ in the Presence of Chloroacetic Acid Salt

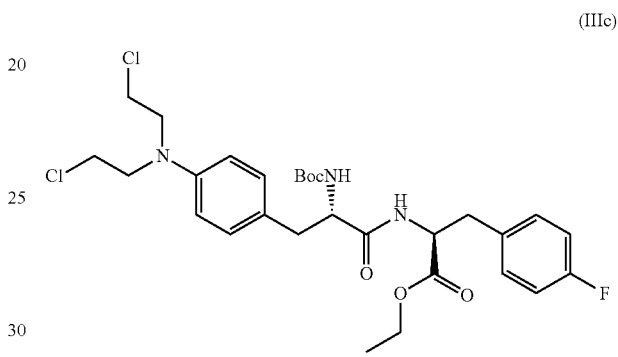

In a 0.5 L dried reactor with overhead stirrer, compound (IIc) (6.99 g, 14.76 mmol) was added, followed by anhydrous tetrahydrofuran (46 mL), chloroacetic acid (36.3 g, 383.8 mmol), chloroacetic acid sodium salt (17.2 g, 147.6 mmol) at $T_J$=5-13° C. A solution of BH$_3$SMe$_2$ (14.6 g, 191.9 mmol, 18.2 mL) was then added over 45 minutes. After the addition, the reaction temperature was adjusted to $T_J$=25-30° C. and kept for 2 hr after reaching this temperature. The reaction was slowly quenched with ethanol (17.7 g, 383.8 mmol, 22.4 mL) and was stirred overnight at $T_J$=5° C. and then slowly diluted with distilled water (138 mL) to precipitate the product, compound (IIIc). The temperature was adjusted to $T_1$=15° C. and the stirring rate was increased before addition of a solution of aqueous K$_2$CO$_3$ (8.0 M, 27 mL) to pH=7.0-7.5. The reaction slurry was collected on a filter and reaction vessel and filter-cake were washed with water (2×40 mL). The filter-cake was re-slurred in water (200 mL) for 1 hr at $T_J$=20° C. and then filtered again. Washing with water (50 mL), followed by drying at $T_J$=35° C. under high vacuum, produced the crude white product, compound (IIIc), in 7.85 g (88.8%) uncorrected yield. HPLC purity 97.5 area %.

Crude compound (IIIc) (7.5 gram) prepared according to the described procedure was charged to a reactor and washed down with 2-MeTHF (80 mL). Heating at $T_J$=50° C. dissolved the substance. Heptane (80 mL) was added with stirring at $T_J$=45-50° C. and then stirred before adjusting the temperature to $T_J$=10° C. The precipitated solid was collected by filtration and dried at $T_J$=35° C. under high vacuum which produced white product, compound (IIIc), in 6.86 g (91.5%). HPLC purity 99.1 area %.

$^1$H-NMR (300 MHz, DMSO-D$_6$) δ 8.30 (1H, d, J=7.8 Hz), 7.26 (2H, dd, J=8.1, 6 Hz), 7.09-7.05 (3H, m), 6.79 (1H, d, J=8.9 Hz), 6.63 (2H, d, J=8.4 Hz), 4.49-4.42 (1H, dd, J=14.7, 7.5 Hz), 4.07-3.99 (3H, m), 3.68 (8H, s), 3.06-2.91

(2H, m), 2.76 (1H, dd, J=13.8, 4.2 Hz), 2.56 (1H, m), 1.29 (9H, s), 1.1 (3H, t, J=6.6 Hz)

$^{13}$C-NMR (75 MHz, DMSO-D$_6$) δ 172.1 (C=O), 171.3 (C=O), 161.2 (C—F, d, J=242.3 Hz), 155.2 (C=O), 144.7 (C), 133.2 (C, d, J=3.0 Hz), 131.1 (2 carbon, CH, d, J=7.5 Hz), 130.2 (2 carbon, CH), 126.1 (C), 114.9 (2 carbon, CH, J=21.1 Hz), 111.6 (2 carbon, CH), 78.0 (C), 60.6 (CH$_2$), 55.9 (CH), 53.5 (CH), 52.2 (CH$_2$), 41.2 (CH$_2$), 36.4 (CH$_2$), 35.9 (CH$_2$), 28.1 (3 carbons, CH$_3$), 14.0 (CH$_3$)

(ii) Carried Out Using BH$_3$SMe$_2$ in the Presence of Chloroacetic Acid Salt

In a 0.5 L dried reactor with overhead stirrer, compound (IIc) (7.5 g, 15.84 mmol) was added, followed by 2-MeTHF (150 mL). The mixture was heated to 45° C. to form a clear solution. The solution was cooled to 4° C. and chloroacetic acid (38.9 g, 411.8 mmol), followed by chloroacetic acid sodium salt (18.4 g, 158.4 mmol) was added at T$_j$=5-13° C. A solution of BH$_3$SMe$_2$ (15.6 g, 205.9 mmol, 19.5 mL) was then added over 90 minutes. After the addition, the reaction temperature was adjusted to T$_j$=20-25° C. and kept for 5 hr after reaching this temperature. The reaction was slowly quenched with water at T$_j$=15-25° C. (150 g, 8333 mmol, 150 mL), pH=3.5 in water phase, and left overnight without stirring at T$_j$=6° C. Product, compound (IIIc), had precipitated out in the organic phase and the temperature was adjusted to T$_j$=35° C. while stirring, and two clear phases formed. The phases were allowed to separate and the water phase was removed. The organic phase was washed three times with 20% NaCl(aq). pH in the three water phases were: 1.7, 1.1, and 1.1. After the removal of the third water phase, the organic phase was transferred to a round bottom flask and concentrated to half its volume on an evaporator. Product, compound (IIIc), started to precipitate out and the product slurry was allowed to mature at 6° C. for 19 hr. The slurry was collected on a filter and round bottom flask and filter-cake were washed with 2-MeTHF:n-heptane (2×40 mL), followed by drying at T$_j$=35° C. under high vacuum, to produce the crude white product, compound (IIIc), in 8.3 g (87.6%) uncorrected yield. HPLC purity 99.4 area %.

(iii) Carried Out Using Borane-Tetrahydrofuran in the Presence of Chloroacetic Acid Salt In a 100 mL dried round bottom flask with magnet stirrer bar, compound (IIc) (0.75 g, 1.58 mmol) was added under a slow nitrogen flow followed by anhydrous tetrahydrofuran (6 mL), chloroacetic acid (3.89 g, 41.2 mmol), and chloroacetic acid sodium salt (1.84 g, 15.8 mmol). At T$_j$=5-13° C. ° C. a 1 M solution of BH$_3$THF (20.6 mmol, 20.6 mL) was added over 30 minutes. After the addition the reaction temperature was adjusted between T$_j$=23-28° C. and kept for 2 hr after reaching this temperature. In process control sample (HPLC) indicated in-complete reaction and the jacket temperature was set to T$_j$=40° C. and when the internal temperature reached T$_j$=40° C. the reaction was kept at this temperature for 2 hr when in-process sample (HPLC) showed 6.7 area % starting material, 7.1% acylation adduct (impurity) and 84.1% compound (IIIc). The reaction was progressed at T$_j$=23° C. and left for 4 days before slowly quenched with ethanol (2.4 g, 3 mL). Water (100 mL) was added and the pH adjusted with 1 M aqueous K$_2$CO$_3$ to pH 7. The reaction slurry was collected on a filter and reaction vessel and filter-cake were washed with water (2×20 mL) followed by drying at T$_j$=35° C. under high vacuum produced the crude colorless product in 0.85 g (89.6%) uncorrected yield. HPLC purity was 94.3 area %, with one major impurity attributed to a chloroacylation adduct of the starting material in 3.8 area %.

(iv) Carried Out Using BH$_3$SMe$_2$ without Addition of Chloroacetic Acid Salt

In a 100 mL dried round bottom flask with magnet stirrer bar, compound (IIc) (0.75 gram, 1.58 mmol) was added under a slow nitrogen flow followed by anhydrous tetrahydrofuran (6 mL) and chloroacetic acid (3.89 g, 41.2 mmol). At T$_j$=5-16° C. a solution of BH$_3$SMe$_2$ (1.56 g, 20.6 mmol, 2.0 mL) was added over 30. After the addition the reaction temperature was adjusted between T$_j$=25° C. and kept for 2.5 h after reaching this temperature. A process control sample (HPLC) indicated melflufen (Compound (Ib)), the Boc-deprotected form of Compound (IIIc), in 66 area %. The reaction was slowly quenched with ethanol (2.9 g, 3.7 mL). The pH of the reaction was adjusted with 1 M aqueous K$_2$CO$_3$ solution to pH=8, followed by addition of EtOAc (40 mL). Layers were separated and the aqueous layer re-extracted with EtOAc (50 mL). The organic layers were combined and reduced at <30 mbar/35° C. to an oil. The oil was re-distilled from EtOAc (30 mL) twice and the residue was dried at T$_j$=23° C./5 mbar to leave 1.6 g brownish oil. HPLC purity of Compound (Ib) was 66.1 area %.

Example 4—Preparation of Compound (Ib) as Hydrochloride Salt

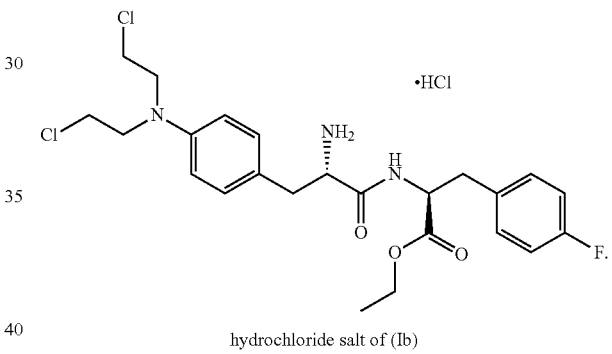

hydrochloride salt of (Ib)

Boc-melflufen (compound (IIIc)) (5.0 g, 8.3 mmol) was charged to a round bottomed flask, equipped with magnet stirrer bar, and nitrogen inlet. 1.3 M HCl (anhydrous) in ethanol (64 mL, 83.5 mmol, 10 eq.) was added. After 19 h the conversion was 99.4%. The solvents were partially distilled at T$_j$=33° C. on a rotary evaporator, followed by the addition of ethanol (18 mL). This was repeated twice. Seed crystals were added and after 30 minutes product had precipitated. The slurry was stirred for 21 h and was then concentrated. Methyl tert-butyl ether (MTBE) (108 mL) was added at room temperature with an even rate over 30 minutes. After 100 minutes of stirring at room temperature the precipitate was collected by vacuum filtration and washed with 2×25 mL ethanol:MTBE (1:6). Drying was performed overnight at T$_j$=35° C./5 mbar in vacuum oven. Yield of compound (Ib) in the form of its hydrochloride salt, 4.0 g (90%). HPLC-purity 98.7 area %.

$^1$H-NMR (300 MHz, MeOH-D$_4$) δ 7.26 (2H, dd, J=8.4, 8.1 Hz), 7.17 (2H, d, J=8.4 Hz), 7.02 (2H, dd, J=9, 8.4 Hz), 6.74 (2H, d, J=8.4 Hz), 4.69 (1H, dd, J=7.8, 6.3 Hz), 4.15 (2H, dd, J=14.1, 7.2 Hz), 4.04 (1H, dd, J=8.4, 5.4 Hz), 3.76 (4H, dd, J=6.3, 6 Hz), 3.67 (4H, dd, 6.6, 5.7 Hz), 3.17 (2H, dd, J=14.4, 6 Hz), 3.06-2.88 (2H, m), 1.22 (3H, t, J=7.2 Hz)

$^{13}$C-NMR (75 MHz, MeOH-D$_4$) δ 172.2 (C=O), 169.8 (C=O), 163.4 (C—F, d, J=244.5 Hz), 147.4 (C), 133.9 (C, d, J=3 Hz), 132.1 (2 carbon, CH, d, J=7.5 Hz), 131.8 (2 carbon, CH), 123.4 (C), 116.2 (2 carbon, CH, d, J=21.9 Hz), 113.7 (2 carbon, CH), 62.6 (CH$_2$), 55.6 (CH), 55.5 (CH), 54.3 (CH$_2$), 41.6 (CH$_2$), 37.6 (CH$_2$), 37.6 (CH$_2$), 14.5 (CH$_3$)

Example 4 was repeated successfully in the presence ethyl acetate and with varying concentrations of HCl from 1.3 M to 2.5 M and at varying temperatures from 6° C. to room temperature.

The invention claimed is:

1. A process for the production of compound (III):

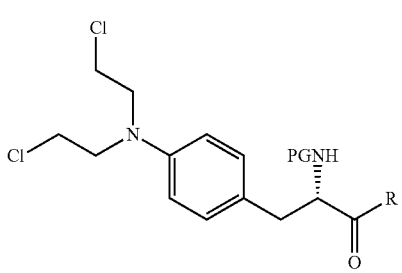

comprising reacting compound (II)

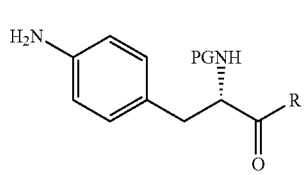

with chloroacetic acid, in the presence of a reducing agent and a chloroacetate salt buffering agent;
wherein PG is a protecting group and R is OH in a suitably protected form or

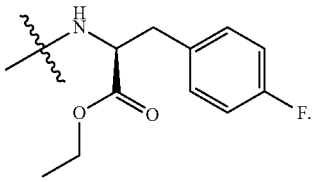 [SMILES: *N[C@@H](Cc1ccc(F)cc1)C(=O)OCC]

2. The process of claim 1, wherein the reducing agent is selected from the group consisting of borane, a borane-Lewis base complex, a borohydride, a metal hydride, and H$_2$ in the presence of a metal catalyst.

3. The process of claim 2, wherein the reducing agent is BH$_3$ or borane dimethylsulfide.

4. The process of claim 1, wherein PG is selected from the group consisting of methyl oxycarbonyl, ethyl oxycarbonyl, 9-fluorenylmethyl oxycarbonyl, t-butyl oxycarbonyl, benzyl oxycarbonyl, p-methoxybenzyl oxycarbonyl, 1-adamantyl oxycarbonyl, p-bromobenzyl oxycarbonyl, trifluoroacetyl, chloroacetyl, phenylacetyl, benzacetyl, p-toluenesulfonyl, 2-nitrobenzenesulfonyl, t-butylsulfonyl, 2- or 4-nitrobenzenesulfonyl, 2,4-dinitrobenzenesulfonyl, and 2-naphthalenesulfonyl.

5. The process of claim 4, where PG is t-butyl oxycarbonyl.

6. The process of claim 1, which is performed at a temperature in the range of from 3 to 50° C.

7. The process of claim 1, wherein the molar ratio of chloroacetic acid:the chloroacetate salt is from 2:1 to 5:1.

8. The process of claim 1, wherein the molar ratio of chloroacetic acid:the chloroacetate salt is from 1:7 to 1:20.

9. The process of claim 1, wherein R is

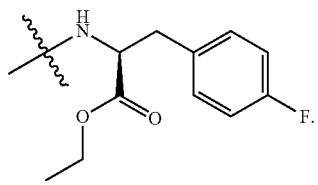 [SMILES: *N[C@@H](Cc1ccc(F)cc1)C(=O)OCC]

10. The process of claim 1, further comprising a step of forming a salt of compound (III).

11. The process of claim 1, further comprising a step of producing compound (II), comprising reacting compound (VI):

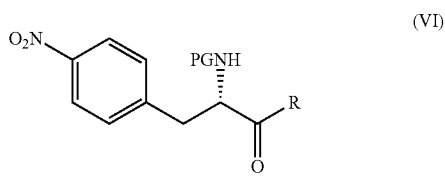

with a reducing agent,
wherein PG is as defined for compound (II) and R is OH in a suitably protected form or

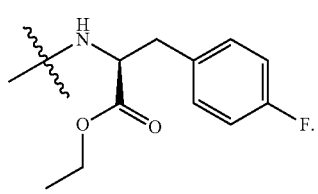

12. The process as claimed in claim 11, wherein the reducing agent used to produce compound (II) from compound (VI) in the step recited in claim 11 is hydrogen and a catalyst.

13. The process of claim 11, wherein R is

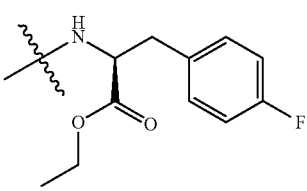 [SMILES: *N[C@@H](Cc1ccc(F)cc1)C(=O)OCC]

and further comprising a step of producing compound (VI) by reacting compound (IV):

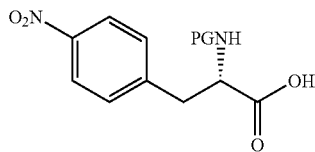

with compound (V):

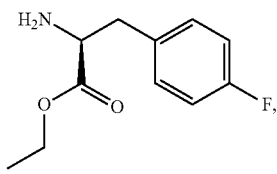

wherein PG is as defined for compound (II).

14. The process of claim 1, further comprising deprotecting compound (III) to produce compound (I), or a salt thereof:

(I)

wherein R is OH optionally in a suitably protected form or

15. The process as claimed in claim 14, wherein compound (I) is compound (Ib), or a salt thereof:

(Ib)

16. The process of claim 14, wherein compound (I) is produced from the deprotection step and further comprising a step of forming a salt of compound (I).

17. The process of claim 16, wherein the salt of compound (I) is:

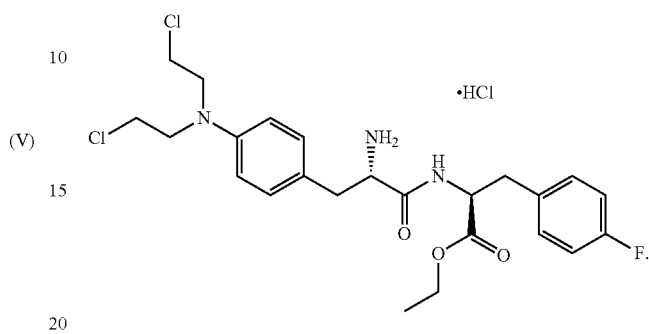

18. A process for the production of compound (VIb):

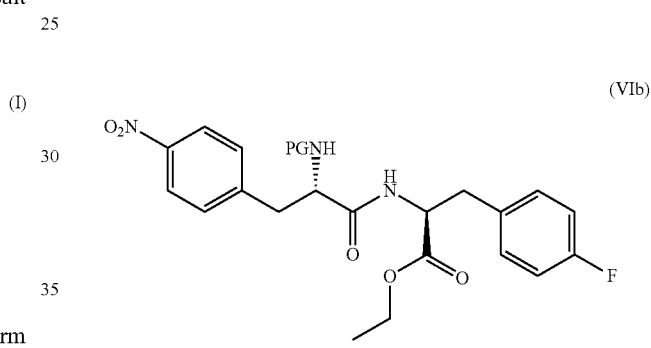

comprising reacting compound (IV):

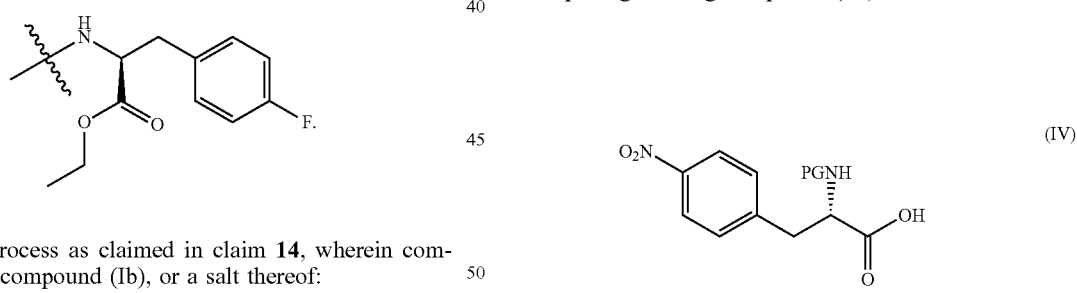

with compound (V):

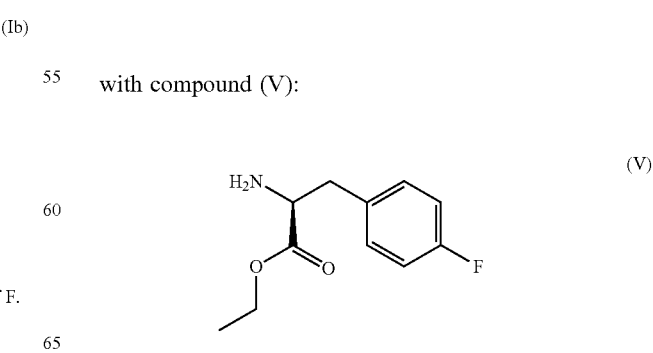

wherein PG is a protecting group.

19. A compound having the following structure:

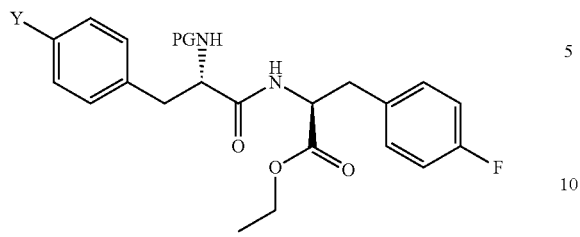

wherein Y is $NH_2$ or $NO_2$, and PG is a protecting group.

20. The compound of claim 19, wherein PG is t-butyl oxycarbonyl.

21. The process of claim 1, which is performed at a temperature in the range of from 4 to 45° C.

22. The process of claim 1, which is performed at a temperature in the range of from 5 to 40° C.

23. The process of claim 1, wherein the chloroacetate salt is sodium chloroacetate.

24. The process of claim 12, wherein the catalyst is Pd/C.

25. The process of claim 1, further comprising a step of forming a hydrochloride salt of compound (III).

26. The process of claim 14, wherein compound (I) is produced from the deprotection step and further comprising a step of forming a hydrochloride salt of compound (I).

* * * * *